United States Patent
Hernandez et al.

(10) Patent No.: US 11,690,621 B2
(45) Date of Patent: Jul. 4, 2023

(54) PERCUTANEOUS CLIP FOR REPAIRING A HEART VALVE

(71) Applicant: Edwards Lifesciences Corporation, Irvine, CA (US)

(72) Inventors: Cristobal R. Hernandez, Santa Ana, CA (US); Gregory Bak-Boychuk, San Clemente, CA (US); Emil Karapetian, Huntington Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 903 days.

(21) Appl. No.: 16/663,241

(22) Filed: Oct. 24, 2019

(65) Prior Publication Data

US 2020/0054335 A1    Feb. 20, 2020

Related U.S. Application Data

(63) Continuation of application No. 14/959,903, filed on Dec. 4, 2015, now Pat. No. 10,524,792.
(Continued)

(51) Int. Cl.
*A61B 17/08* (2006.01)
*A61B 17/122* (2006.01)
(Continued)

(52) U.S. Cl.
CPC ............ *A61B 17/083* (2013.01); *A61B 17/10* (2013.01); *A61B 17/1227* (2013.01);
(Continued)

(58) Field of Classification Search
CPC ..... A61B 17/083; A61B 17/10; A61B 17/122; A61B 17/1227; A61B 17/1285;
(Continued)

(56) References Cited

U.S. PATENT DOCUMENTS

| 3,874,388 A | 4/1975 | King et al. |
| 4,340,091 A | 7/1982 | Skelton et al. |

(Continued)

FOREIGN PATENT DOCUMENTS

| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Ashley L Fishback
(74) *Attorney, Agent, or Firm* — Thomas C. Richardson

(57) ABSTRACT

Valve repair systems and clips for attachment to one or more leaflets of a heart valve. The clip can include an elongated member configured to be positioned between two leaflets of the heart valve. The elongated member can have a first portion and a second portion that extends from the first portion. A width of the second portion can be greater than the width of the first portion. A pair of arms can be coupled to the first portion and extend toward the second portion. The pair of arms can extend radially away from the elongated member as the pair of arms extend away from the first portion toward the second portion when the arms are in an open position. And the pair of arms can be moveable from the open position to a closed position to pinch each leaflet between one of the arms and the elongated member.

15 Claims, 19 Drawing Sheets

Related U.S. Application Data

(60) Provisional application No. 62/087,530, filed on Dec. 4, 2014.

(51) Int. Cl.
*A61F 2/24* (2006.01)
*A61B 17/128* (2006.01)
*A61B 17/10* (2006.01)
*A61B 17/00* (2006.01)
*A61B 17/064* (2006.01)

(52) U.S. Cl.
CPC ........ *A61B 17/1285* (2013.01); *A61F 2/2463* (2013.01); *A61B 2017/00243* (2013.01); *A61B 2017/00349* (2013.01); *A61B 2017/0649* (2013.01)

(58) Field of Classification Search
CPC . A61B 2017/00243; A61B 2017/00349; A61F 2/24; A61F 2/2463
See application file for complete search history.

(56) References Cited

U.S. PATENT DOCUMENTS

| | | | |
|---|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,592 B2 | 11/2011 | Goldfarb et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |

(56) References Cited

U.S. PATENT DOCUMENTS

| | | |
|---|---|---|
| 8,876,895 B2 | 11/2014 | Tuval et al. |
| 8,945,177 B2 | 2/2015 | Dell et al. |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0120341 A1 | 6/2003 | Shennib et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0080440 A1 | 4/2005 | Durgin et al. |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0064118 A1 | 3/2006 | Kimblad |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0174363 A1 | 7/2010 | Castro |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |

(56) References Cited

U.S. PATENT DOCUMENTS

| | | |
|---|---|---|
| 2013/0190798 A1 | 7/2013 | Kapadia |
| 2013/0190861 A1 | 7/2013 | Chau et al. |
| 2013/0226199 A1 | 8/2013 | Harris et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0222136 A1 | 8/2014 | Geist et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0092661 A1 | 4/2018 | Prabhu |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik |
| 2020/0360054 A1 | 11/2020 | Walsh et al. |
| 2020/0360132 A1 | 11/2020 | Spence |

(56) References Cited

U.S. PATENT DOCUMENTS

| | | |
|---|---|---|
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0313433 A1 | 10/2022 | Ma et al. |
| 2023/0014540 A1 | 1/2023 | Metchik et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2009091509 A1 | 7/2009 |
| WO | 2014034254 A1 | 3/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Andersen et al., "Transluminal Implantation of Artificial Heart Valves. Description of a New Expandable Aortic Valve and Initial Results with Implantation by Catheter Technique in Closed Chest Pigs" European Heart Journal, 1992, 13, 704-708.

Andersen, H.R. "History of Percutaneous Aortic Valve Prosthesis," Herz No. 34. pp. 343-346. 2009.

Batista, M.D. et al., "Partial Left Ventriculectomy to Treat End-Stage Heart Disease," The Society of Thoracic Surgeons, 1997, pp. 634-638.

Beall et al.,"Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et alL., "Improved results with mitral valve repair using new surgical techniques", Eur J Cardiothorac Surg. 1995;Issue9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.

Lawrence, Jr., et al., "Percutaneous Endovascular Graft: Experimental Evaluation", Cardiovascular Radiology 163, pp. 357-360, May 1987.

Maisano et al., 'The edge-to-edge technique: a simplified method to correct mitral insufficiency', Eur J Cardiothorac Surg., vol. 13, Issue—3, pp. 240-245, Mar. 1998.

D. Pavcnik: Development and Initial Experimental Evaluation of a Prosthetic Aortic Valve for Transcatheter Placement; Cardiovascular Radiology (1992) 183, pp. 151-154.

Porstmann et al., "Der Verschluß des Ductus Arteriosus Persistens Ohne Thorakotomie", Thoraxchirurgie Vaskuläre Chirurgie, Band 15, Heft2, Stuttgart, im Apr. 1967, pp. 199-203.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

(56) References Cited

OTHER PUBLICATIONS

Rashkind et al., "Historical Aspects of Interventional Cardiology: Past, Present, and Future", Texas Heart Institute Journal, Interventional Cardiology, pp. 363-367.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vase Interv Radiol 2003; 14:841-853.

Ross, "Aortic Valve Surgery," At a meeting of the Council on Aug. 4, 1966. pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Umaña et al., Bow-tie 'mitral valve repair: an adjuvant technique for ischemic mitral regurgitation', Ann Thorac Surg., vol. 66, Issue—6, pp. 1640-1646, Nov. 1998.

Urban, M.D., Philip, "Coronary Artery Stenting," Editions Medecine et Hygiene, Geneve, 1991, pp. 5-47.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, "Valve Prostheses," Operative Surgery, 4th ed. pp. 415-424. 1986.

Grasso et al., "The Pascal transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

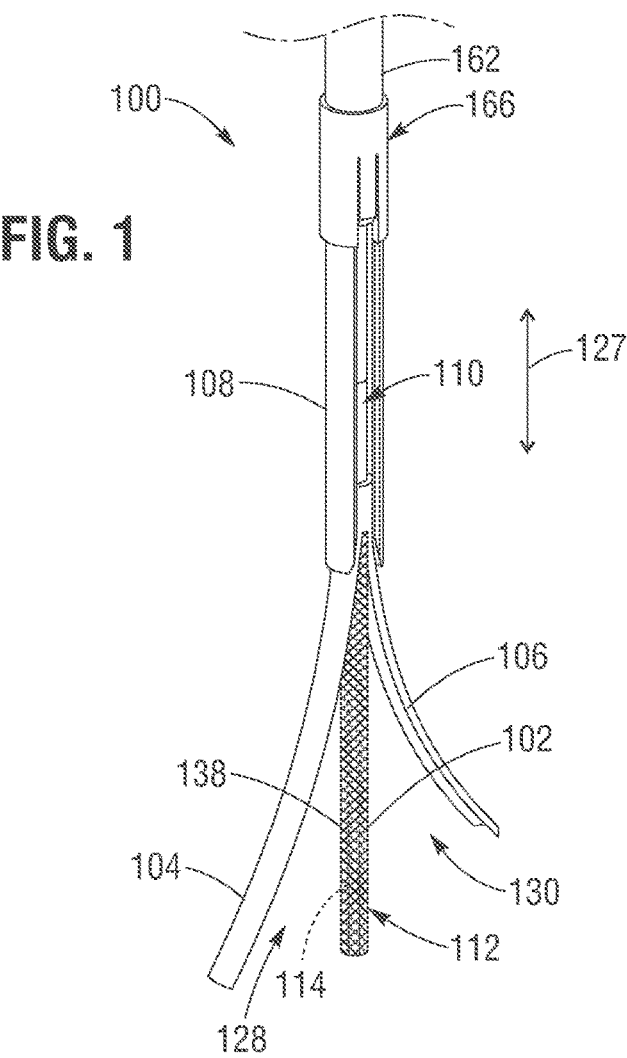
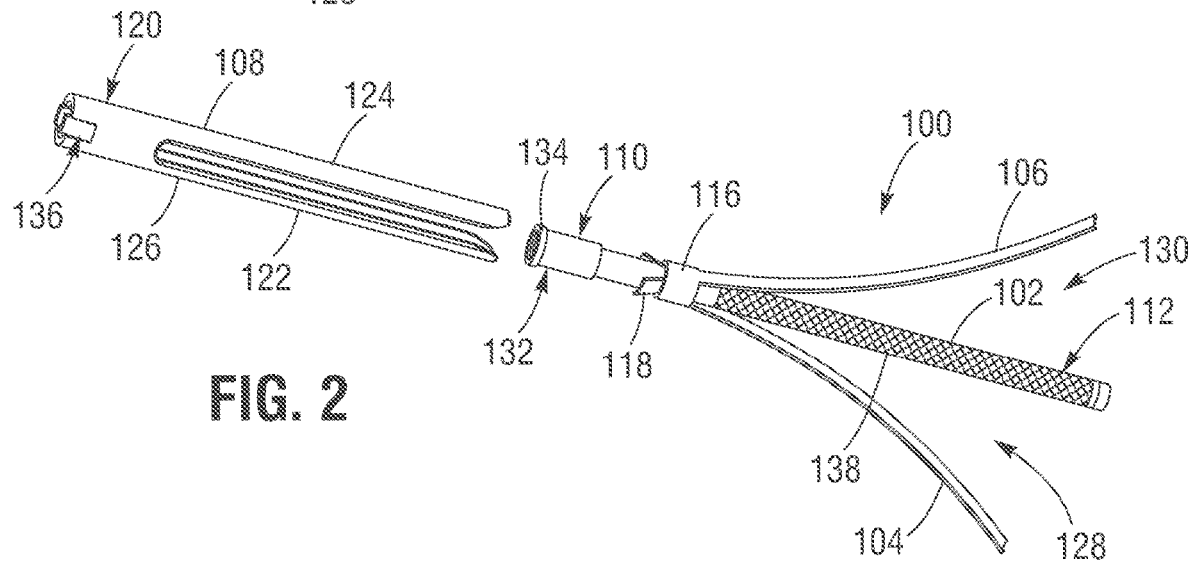

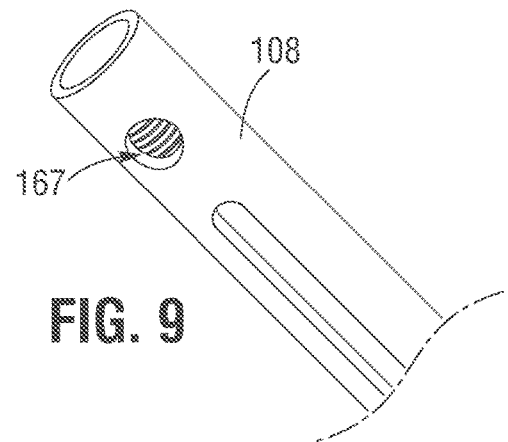
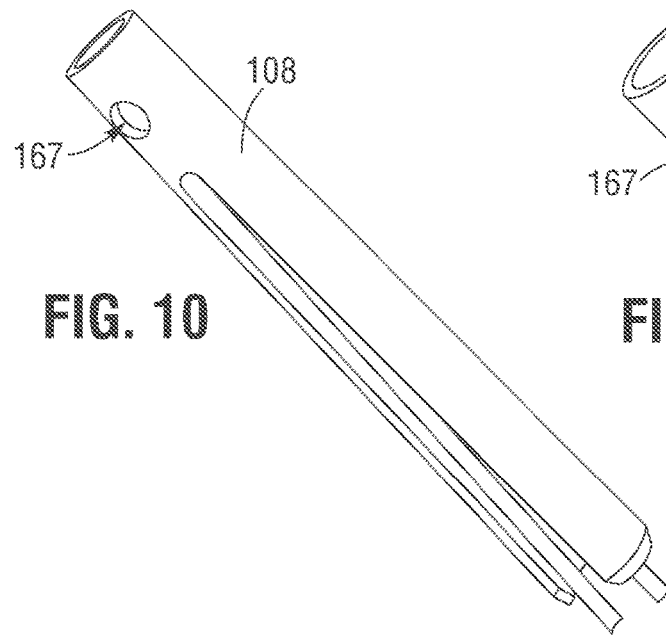
FIG. 10        FIG. 9
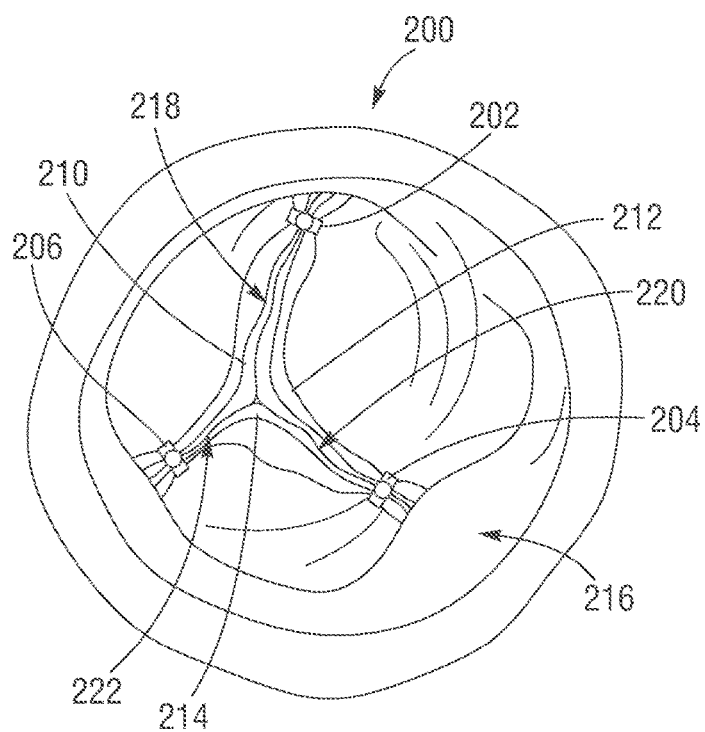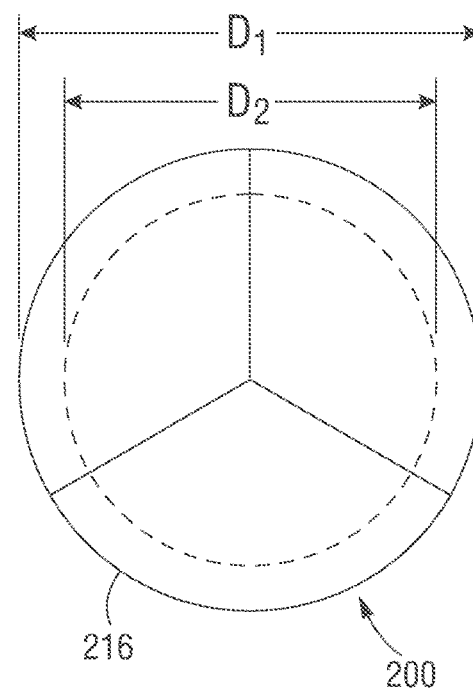
FIG. 11        FIG. 12

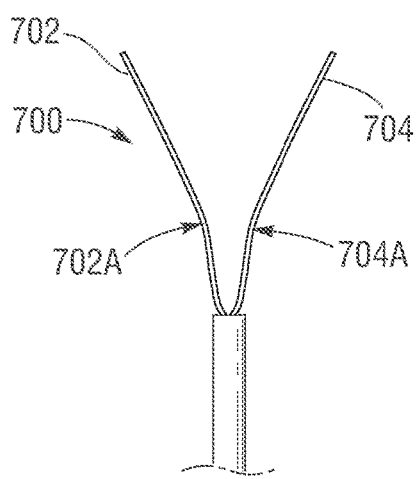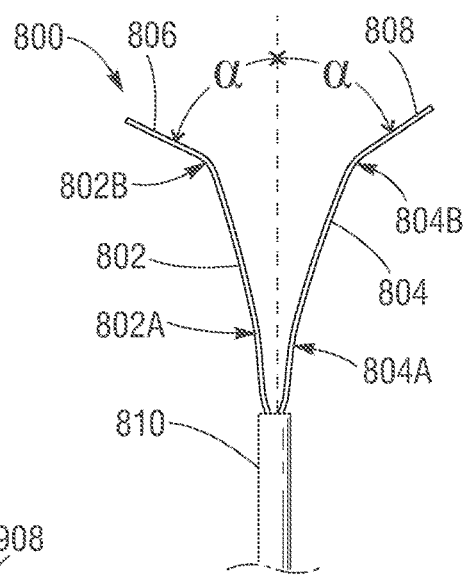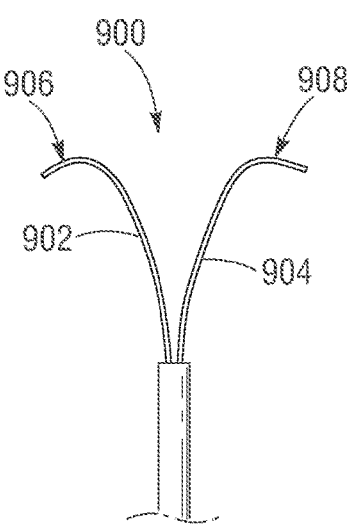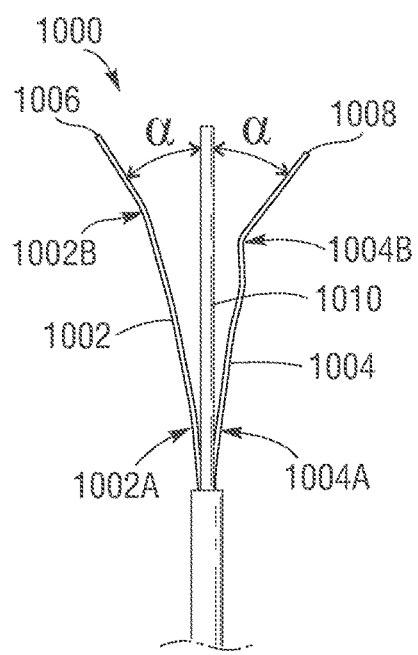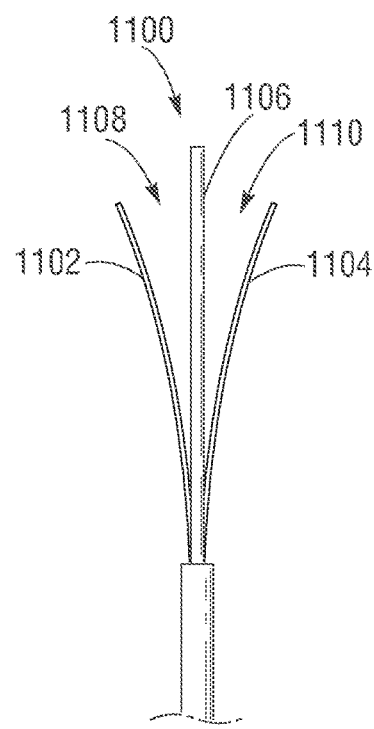
FIG. 24
FIG. 25
FIG. 26
FIG. 27
FIG. 28

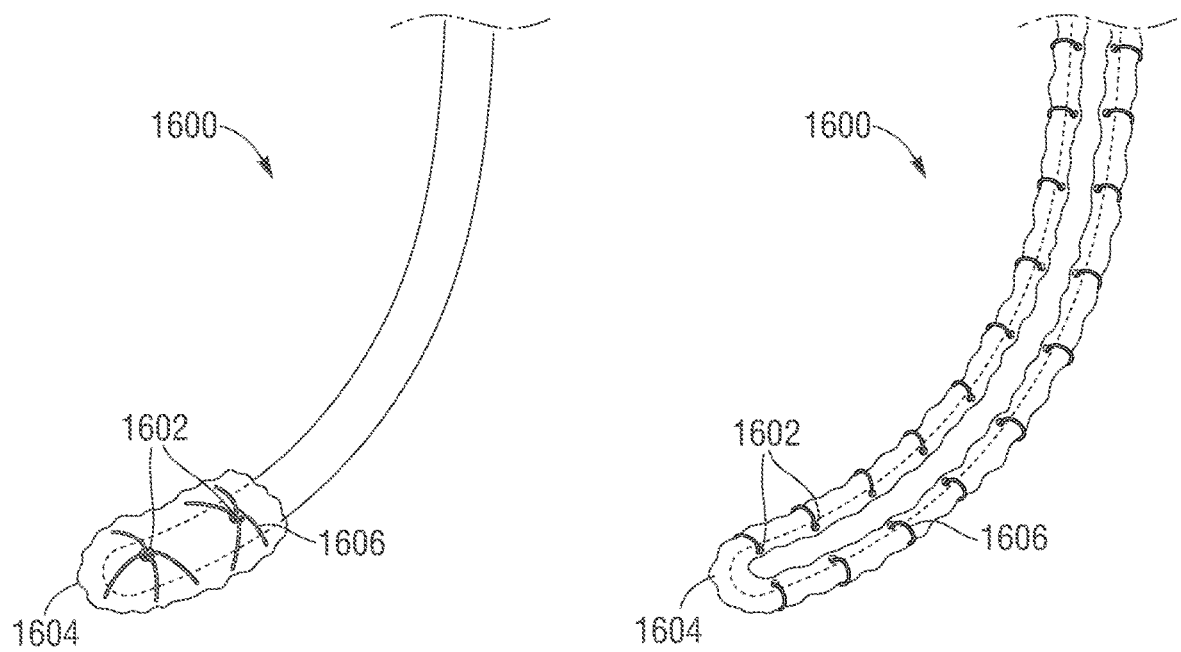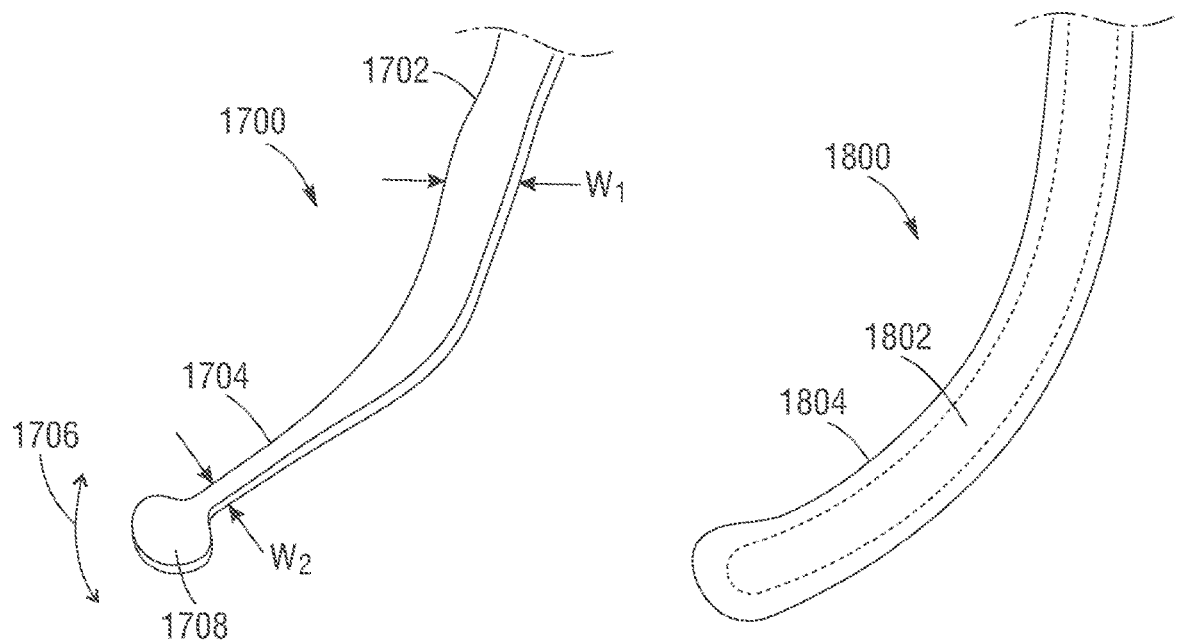

FIG. 39
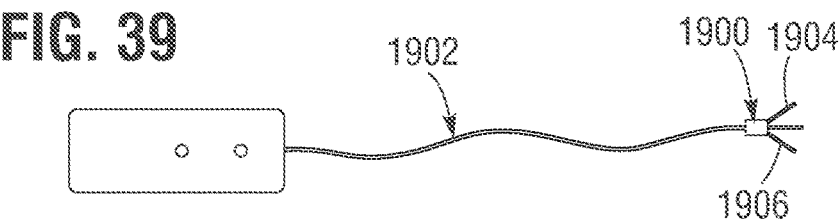
FIG. 40
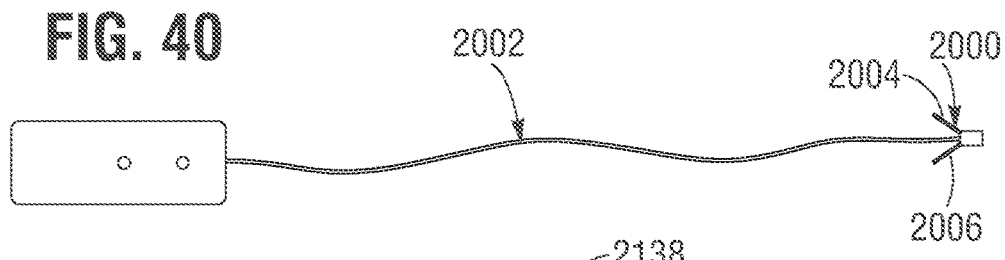
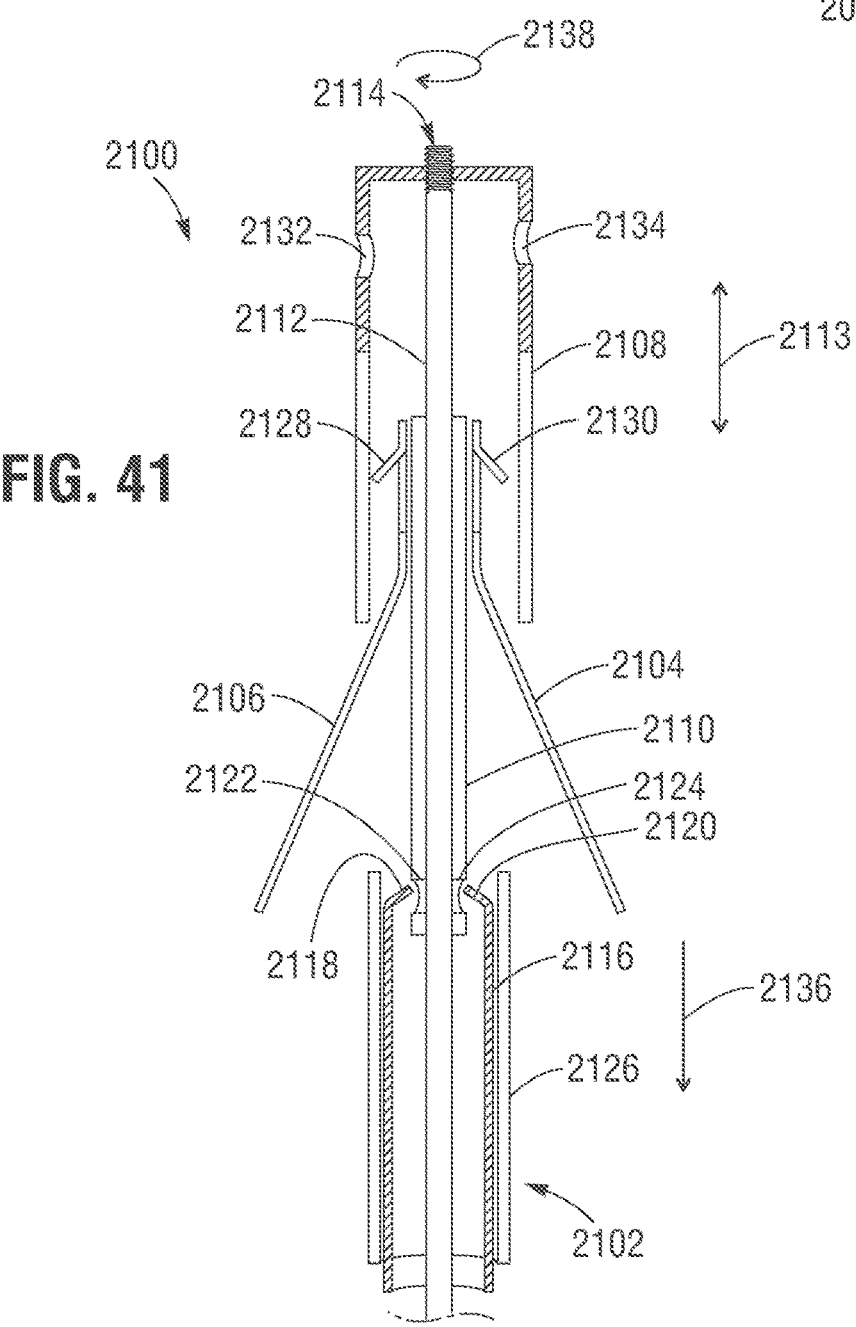
FIG. 41

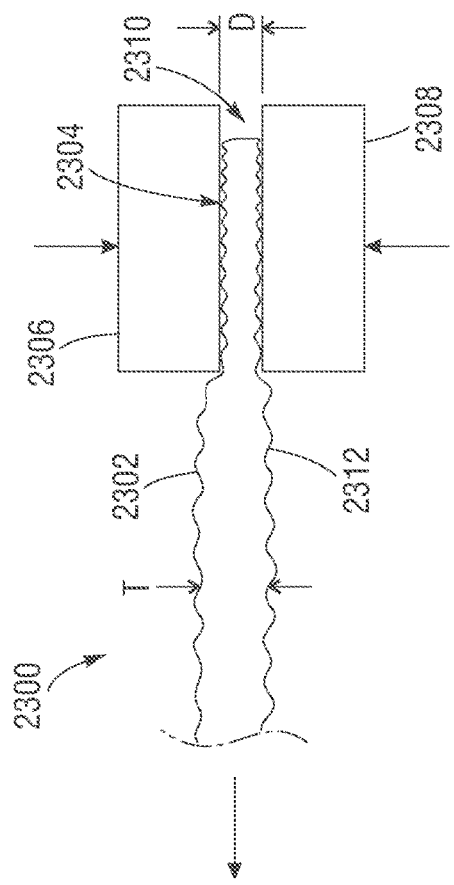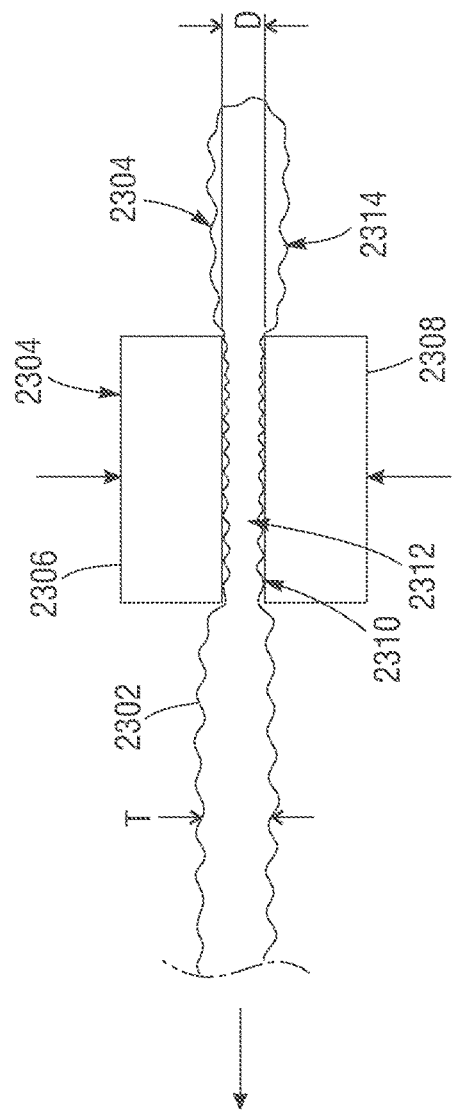

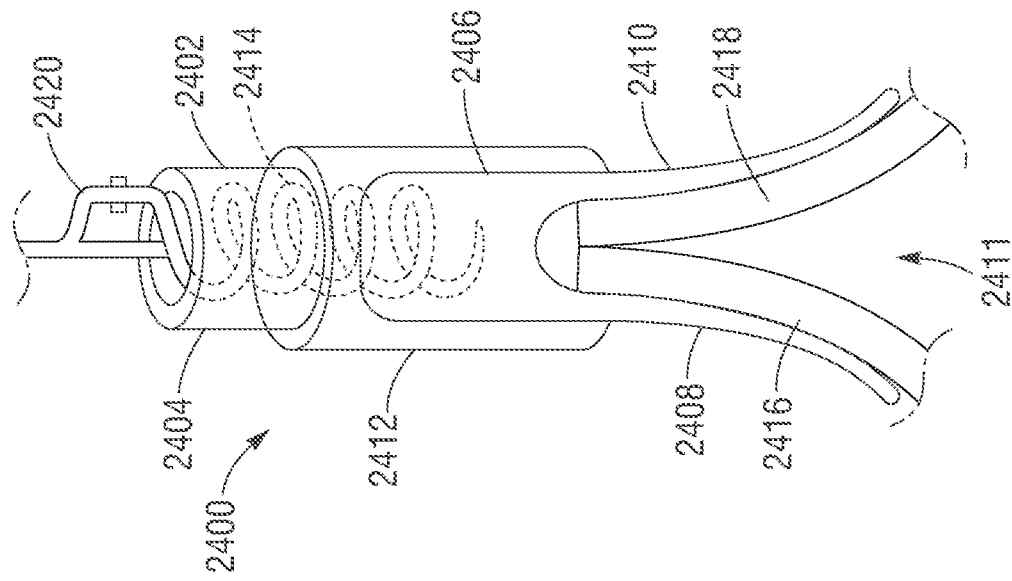
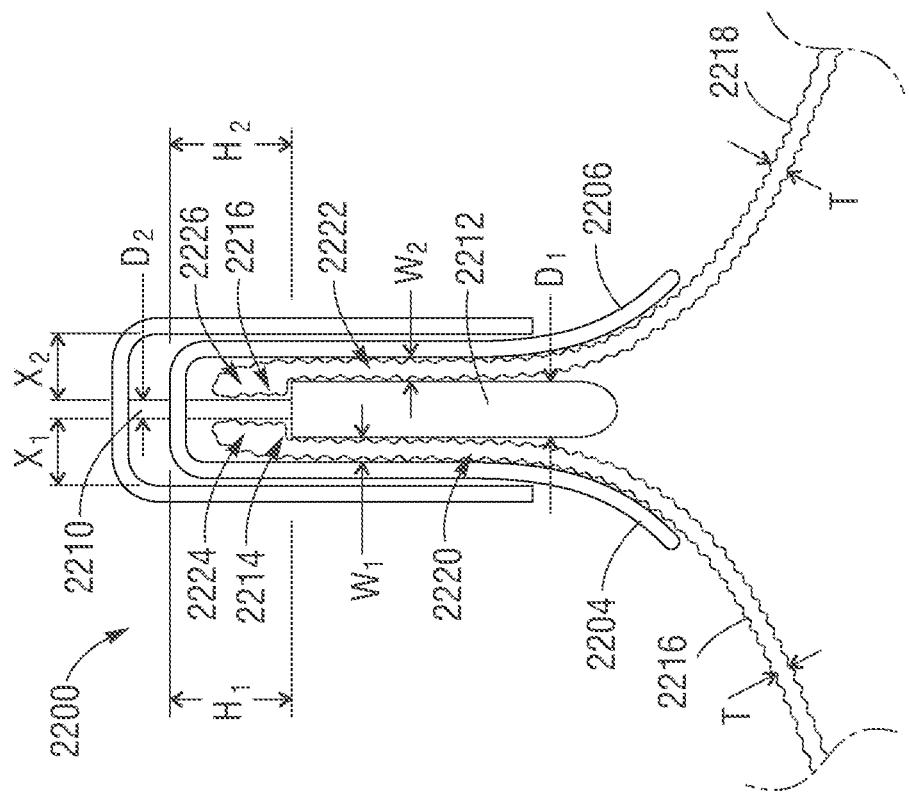

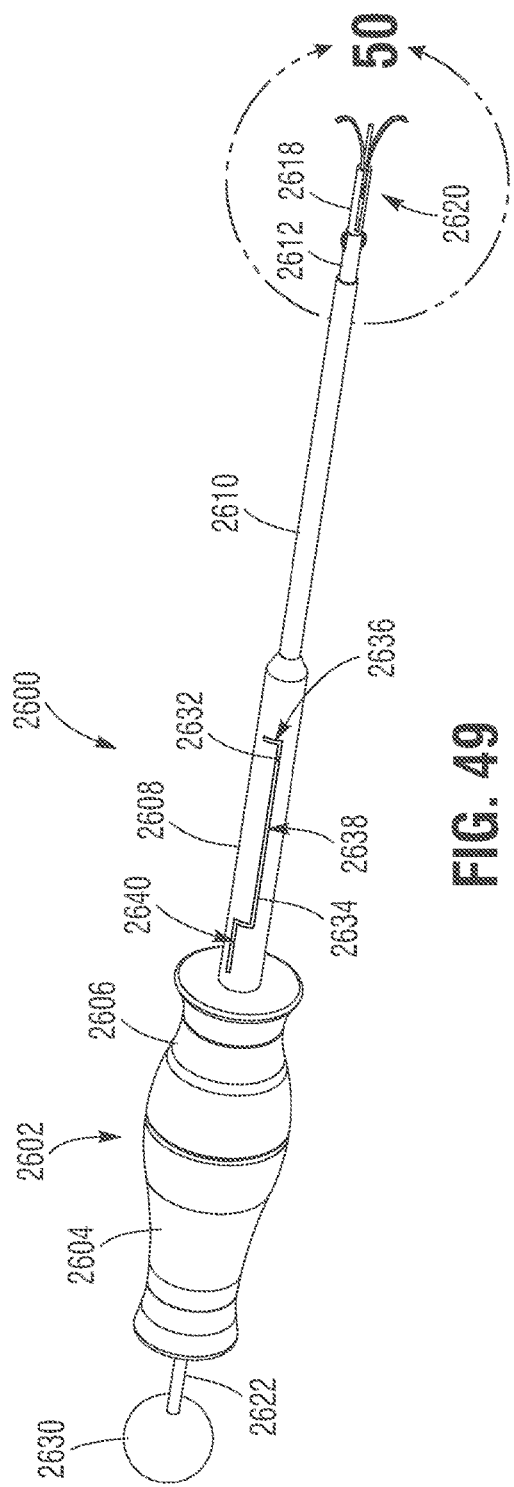
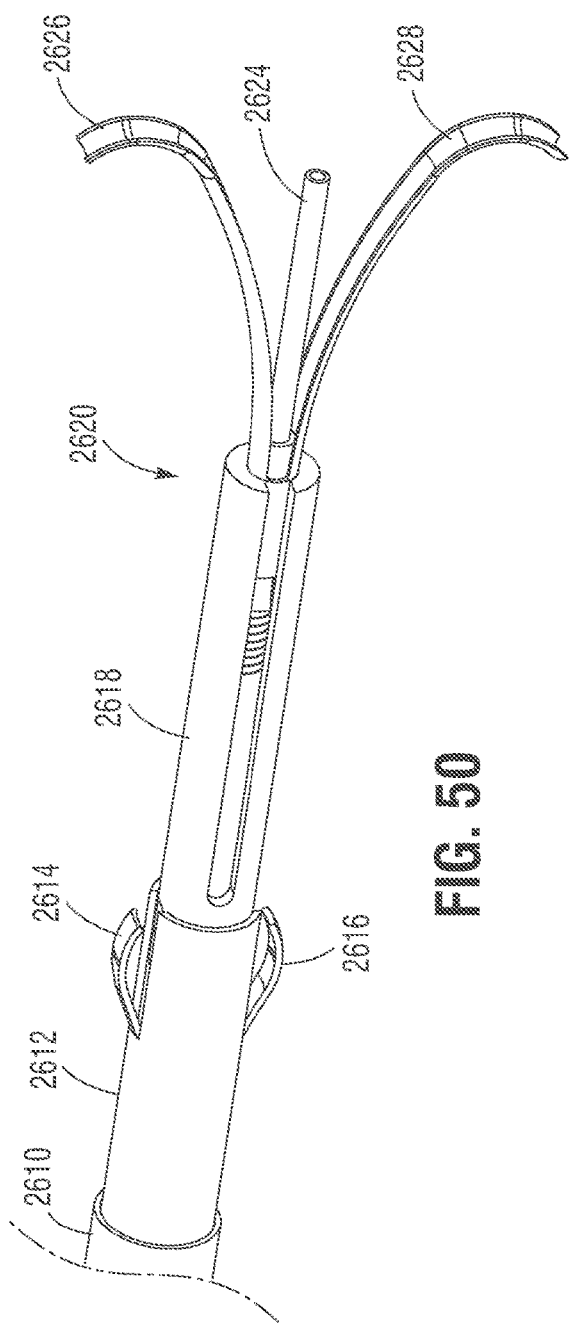
FIG. 49
FIG. 50

PERCUTANEOUS CLIP FOR REPAIRING A HEART VALVE

CROSS REFERENCE TO RELATED APPLICATION

This application is a continuation of U.S. patent application Ser. No. 14/959,903, filed Dec. 4, 2015, which claims the benefit of U.S. Provisional Patent Application No. 62/087,530, filed Dec. 4, 2014, each of which is hereby incorporated herein by reference in its entirety for all purposes.

FIELD

This disclosure relates to devices and methods of treating heart valve insufficiency.

BACKGROUND

Heart valve insufficiency typically involves regurgitation of blood through a heart valve that is unable to close completely or properly, resulting in impaired cardiovascular function. Valvular insufficiency may affect, for example, the mitral valve, the aortic valve, or the tricuspid valve, and can be associated with calcified or prolapsed leaflets, and/or expansion or deformation of the valve annulus. One method of treating heart valve insufficiency is to employ one or more leaflet clips to improve coaptation of the native valve leaflets. However, conventional leaflet clips can be difficult to implant, can interfere with the function of or damage associated valve structures such as chordae, and are frequently limited to use with a single type of heart valve. Accordingly, improvements to devices and methods of treating heart valve insufficiency are desirable.

SUMMARY

Certain embodiments of the disclosure concern leaflet clips and devices and methods of introducing leaflet clips into a heart valve. In one representative embodiment, a leaflet clip comprises an elongated member including a proximal end portion and a distal end portion, and first and second clipping arms movable between an open position and a closed position. The clipping arms include respective proximal end portions coupled to the proximal end portion of the elongated member, and respective distal end portions extending distally and radially outward relative to the elongated member. The leaflet clip further comprises a tubular member coaxially disposed about the elongated member. Axial motion of the tubular member relative to the elongated member or axial motion of the elongated member relative to the tubular member causes corresponding movement of the clipping arms between the open and closed positions.

In another representative embodiment, a method comprises positioning a leaflet clip adjacent a commissure of a heart valve such that a first clipping arm is adjacent a first leaflet of the heart valve and a second clipping arm is adjacent a second leaflet of the heart valve, and an elongated member is positioned between the leaflets. The method further comprises moving a sheath disposed coaxially over the elongated member distally with respect to the elongated member or moving the elongated member proximally with respect to the sheath such that the sheath causes the clipping arms to move from an open position to a closed position, thereby capturing the first leaflet between the first clipping arm and the elongated member and capturing the second leaflet between the second clipping arm and the elongated member.

The foregoing and other objects, features, and advantages of the disclosure will become more apparent from the following detailed description, which proceeds with reference to the accompanying figures.

BRIEF DESCRIPTION OF THE DRAWINGS

FIG. 1 illustrates a perspective view of a representative embodiment of a leaflet clip.

FIG. 2 illustrates a partially exploded view of the leaflet clip of FIG. 1 with the clipping arms in an open position.

FIGS. 9 and 10 illustrate an embodiment of a tubular member disposed in the distal position about an elongated member.

FIG. 11 is a cross-sectional plan view of a heart valve with three leaflet clips implanted in the heart valve.

FIG. 12 is a schematic illustration of a heart valve illustrating a reduction in the diameter of the annulus.

FIGS. 24-32 illustrate various representative configurations of clipping arms of leaflet clips.

FIG. 39 illustrates an embodiment of a leaflet clip coupled to a delivery system with the with the clipping arms of the leaflet clip extending distally relative to the delivery system.

FIG. 40 illustrates an embodiment of a leaflet clip coupled to a delivery system with the clipping arms of the leaflet clip extending proximally relative to the delivery system.

FIG. 41 illustrates another embodiment of a leaflet clip coupled to a delivery system with its clipping arms extending proximally with respect to the delivery system.

FIGS. 44 and 45 schematically illustrate the function of the tissue gathering regions of the leaflet clip of FIG. 42.

FIG. 46 illustrates the leaflet clip of FIGS. 42 and 43 with the clipping arms in the closed position and leaflets disposed in the tissue gathering regions.

FIG. 47 illustrates another embodiment of a leaflet clip including a helical member disposed within a tubular central member.

FIG. 49 is a perspective view of another embodiment of a delivery system that can be used in combination with any of the leaflet clips described herein.

FIG. 50 is an enlarged view of the distal end portion of the delivery device of FIG. 49.

DETAILED DESCRIPTION

Figure 3:
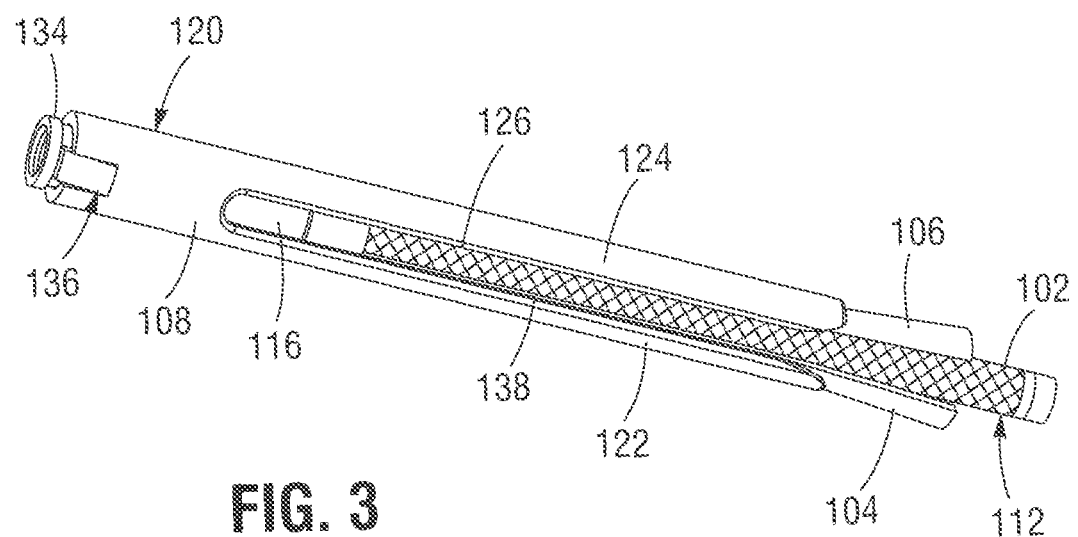
FIG. 3 illustrates a perspective view of the leaflet clip of FIG. 1 with the clipping arms in a closed position.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any disclosed embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

FIGS. 1-3 illustrate a representative embodiment of a leaflet clip 100 including a central elongated member, or shaft, 102, first and second clipping arms 104, 106, and a tubular member 108 (also referred to as a "cover" or "sheath") coaxially disposed over the elongated member 102. The elongated member 102 can have a proximal end portion 110 and a distal end portion 112, and can define a lumen 114 (indicated in phantom in FIG. 1) through which a guide wire can be inserted.

The clipping arms 104, 106 can be coupled to the proximal end portion 110 of the elongated member, and can be movable between an open position (FIGS. 1 and 2) and a closed position (FIG. 3). In the embodiment shown, the clipping arms 104, 106 extend distally from the proximal end portion 110 of the elongated member, and can be shape set such that they curve radially away from the elongated member 102 when in the open position. In some embodiments, the clipping arms 104, 106 can have a curved cross-sectional profile (in a plane perpendicular to the longitudinal axis of the elongated member 102) such that they lay substantially flush against the elongated member 102 when in the closed position.

As shown in FIG. 2, the clipping arms 104, 106 can extend from an annular collar 116 situated coaxially on the proximal end portion 110 of the elongated member 102. In some embodiments, the clipping arms 104, 106 can be integrally formed with the collar 116, or can be separately formed and attached to the collar 116, as desired. For example, in some embodiments, the clipping arms 104, 106 can be hinged. The annular collar 116 can also include one or more radially extending protrusions or tabs 118 extending from the collar 116 and configured to prevent rotation of the tubular member 108 (i.e., "index" the tubular member 108) with respect to the elongated member 102, as further described below. In some embodiments, the clipping arms 104, 106, and/or the collar 116, can be made from any biocompatible material such as, for example, titanium, nickel titanium or nitinol, plastic, stainless steel, etc.

The tubular member 108 can be coaxially disposed over the elongated member 102, and can be axially movable with respect to the elongated member 102 between a first position (FIG. 1) and a second position (FIG. 3), as indicated by arrow 127 of FIG. 1. Referring to FIG. 2, the tubular member 108 can include a proximal end portion 120, and first and second extension portions 122, 124 corresponding to the first and second clipping arms 104, 106. The tubular member 108 can also define slots 126 between the extension portions 122, 124, which can receive the tabs 118 of the collar 116 when the tubular member 108 is in the second position, as shown in FIG. 3. In this manner, as the tubular member 108 moves distally from the first position to the second position, the tabs 118 can travel in the respective slots 126, and the first and second extension portions 122, 124 can contact the first and second clipping arms 104, 106, respectively, and urge the clipping arms 104, 106 into the closed position.

The clipping arms 104, 106 and the elongated member 102 can define respective leaflet receiving regions configured to receive the leaflets of a heart valve when the clipping arms 104, 106 are in the open position. For example, the first clipping arm 104 and the elongated member 102 can define a first leaflet receiving region 128, and the second clipping arm 106 together with the elongated member 102 can define a second leaflet receiving region 130, as shown in FIGS. 1 and 2. During implantation, the leaflet clip 100 can be positioned adjacent a commissure of a heart valve such that one valve leaflet is received in the first leaflet receiving region 128 and a corresponding valve leaflet is received in the second leaflet receiving region 130, while the elongated member 102 extends between the leaflets. In this manner, when the clipping arms 104, 106 are moved from the open position to the closed position, the leaflets can be captured between the first and second clipping arms 104, 106, respectively, and the elongated member 102, as further described below.

In some embodiments, the proximal end portion 110 of the elongated member 102 can include a locking or retaining feature 132 to retain the tubular member 108 in the second position. In the embodiment shown, the retaining feature 132 can comprise a protuberance 134 located on the proximal end of the elongated member 102. The protuberance 134 can have a diameter greater than a diameter of the tubular member 108 such that if the proximal end portion 120 of the tubular member 108 is advanced over the protuberance 134, the protuberance 134 will cause the proximal end portion 120 to expand beyond its natural diameter. Once the proximal end portion 120 of the tubular member 108 is advanced distally of the protuberance 134, the proximal end portion 120 can return to its natural (non-deflected and non-expanded) diameter such that the protuberance 134 restrains proximal movement of the tubular member 108 past the protuberance 134, thereby locking the clipping arms 104, 106 in the closed position.

In this manner, when the leaflet clip 100 has been positioned at a desired location relative to the leaflets of a heart valve, the tubular member 108 can be advanced fully to the second position, locking the tubular member 108 distally of the protuberance 134, and thereby locking the clipping arms 104, 106 in the closed position such that the leaflet clip 100 is retained on the leaflets. In some embodiments, the proximal end portion 120 of the tubular member 108 can define one or more notches 136 to allow the walls of the proximal end portion 120 to flare radially outwardly as they pass over the protuberance 134, thereby allowing the proximal end portion 120 to pass more easily over the protuberance 134. The walls of the proximal end portion 120 can then return to their natural diameter distally of the protuberance 134.

In some embodiments, the leaflet clip 100 can include active or passive leaflet engaging mechanisms, which can be disposed on the elongated member 102, to aid in engaging and retaining the leaflets of a heart valve in the respective first and second leaflet receiving regions 128, 130 as the clipping arms 104, 106 are moved from the open position to the closed position. For example, the leaflet clip 100 can include a passive leaflet engaging mechanism configured as a covering 138 disposed on the distal end portion 112 of the elongated member 102. The covering 138 can have a textured surface such that it can frictionally engage the leaflets when the leaflets are received in the leaflet receiving regions 128, 130, and retain the leaflets in the respective leaflet receiving regions 128, 130 as the clipping arms 104, 106 are moved from the open position to the closed position. In some embodiments, the covering 138 can comprise a woven or braided fabric, or can be a polymeric tube or sleeve configured to be positioned on the distal end portion 112 of the elongated member 102. In some embodiments, the covering 136 can be made of any of various natural or synthetic materials, such as polyethylene terephthalate (PET), foam, silicone, or suture material.

Figure 4:
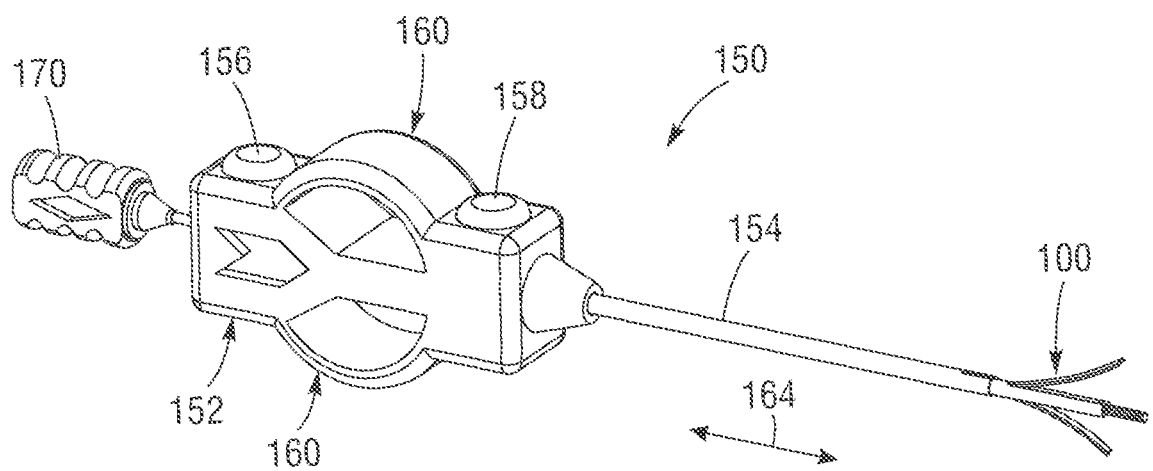
FIG. 4 is a perspective view of a representative embodiment of a delivery system that can be used in combination with the leaflet clip of FIG. 1.
Figure 5:
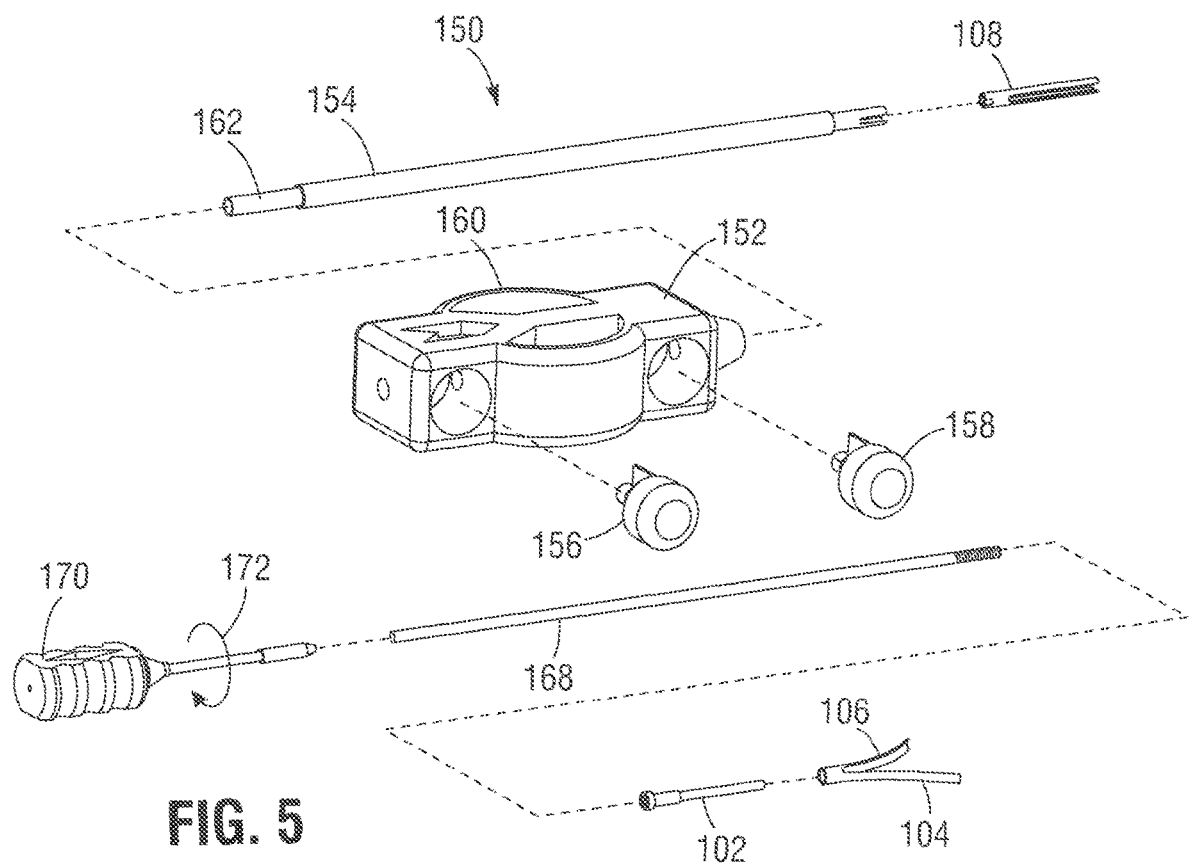
FIG. 5 is an exploded view of the delivery system of FIG. 4.

FIGS. 4 and 5 illustrate the leaflet clip 100 coupled to a representative embodiment of a delivery system 150 that can be used to deliver leaflet clips such as the leaflet clip 100 to a desired heart valve. The delivery system 150 can comprise a main handle body 152 including an outer conduit or shaft 154 movable between a proximal position and a distal position, control buttons 156, 158, and two grip portions 160. Referring to FIG. 5, the delivery system 150 can further include an actuator conduit, or shaft, 162 disposed coaxially within the outer conduit 154 and coupled to the tubular member 108, such that proximal or distal motion of the actuator conduit 162 in the directions indicated by arrow 164 causes corresponding proximal or distal motion of the tubular member 108 with respect to the elongated member 102 and the clipping arms 104, 106.

Figure 6:
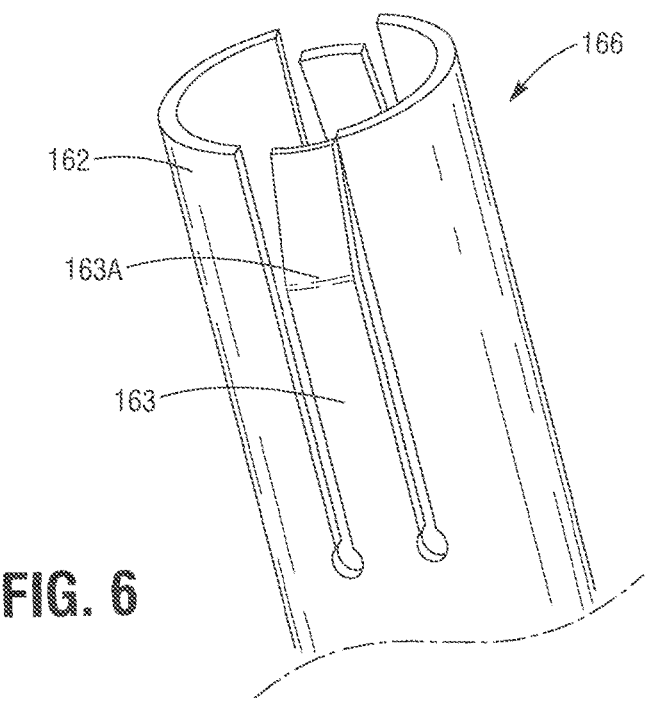
FIGS. 6 and 7 illustrate an embodiment of an actuator conduit.
Figure 7:
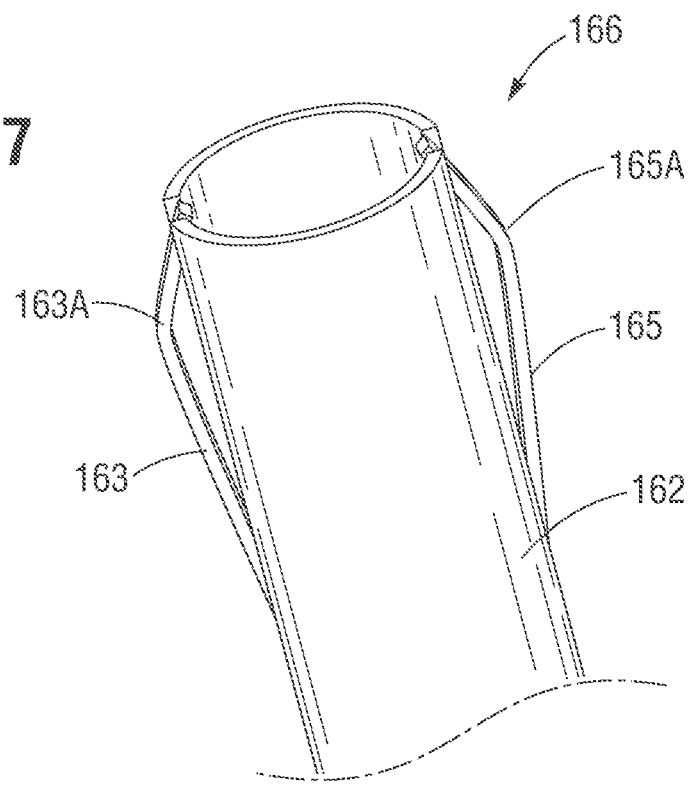
Figure 8:
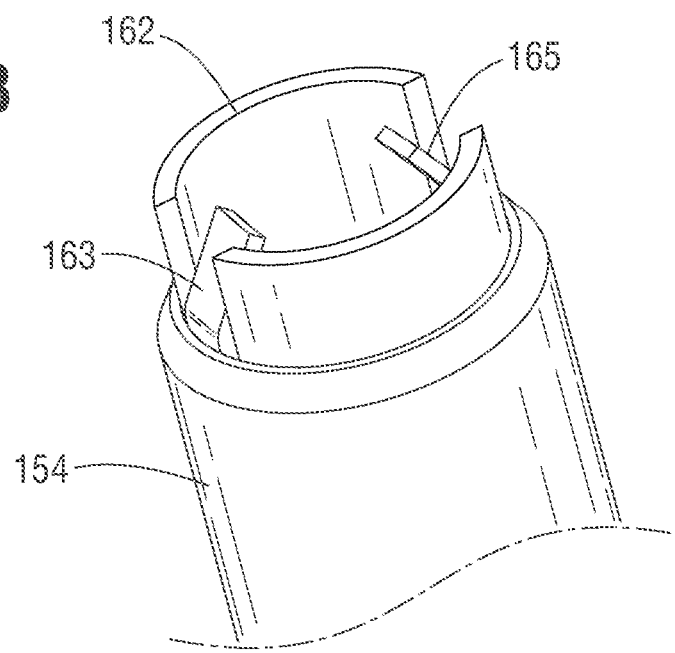
FIG. 8 illustrates an embodiment of an outer conduit disposed coaxially about the actuator conduit of FIG. 6.

In some embodiments, the actuator conduit 162 can include a coupling device 166 to couple the actuator conduit 162 to the proximal end portion 120 of the tubular member 108, as shown in FIGS. 6-8. In some embodiments, the coupling device 166 can comprise a pair of angled tabs 163, 165 coupled to the actuator conduit 162 at their respective proximal ends and shape set such that respective angled portions 163A, 165A of the tabs 163, 165, extend radially beyond the diameter of the actuator conduit 162, as shown in FIG. 7. In this manner, the tabs 163, 165 can act as springs such that when the outer conduit 154 is disposed around the distal end of the actuator conduit 162 (i.e., in the distal position), the inner surface of the outer conduit 154 can contact the angled portions 163A, 165A of the tabs 163, 165 and deflect them radially inward with respect to the actuator conduit 162, as shown in FIG. 8. In this manner, the tabs 163, 165 can extend into respective openings defined in the proximal end portion 120 of the tubular member 108, such as opening 167 shown in FIGS. 9 and 10. This can allow the tabs 163, 165 of the actuator member 162 to releasably engage the tubular member 108 such that proximal and/or distal motion of the actuator conduit 162 causes proximal and/or distal motion of the tubular member 108 and, thereby, movement of the clipping arms 104, 106 between the open and closed positions. In alternative embodiments, the actuator conduit 162 can be coupled to the tubular member 108 by any suitable coupling mechanism, including, for example, threads, clips, a ball and detent system, etc.

Proximal motion of the actuator conduit 162 and, thereby, of the tubular member 108, can be limited by one or more of various controllable motion limiting mechanisms (e.g., cams, hard stops, pull tabs, etc.) to reduce the risk of locking the tubular member 108 in the distal position prior to successful positioning of the leaflet clip 100 (i.e., to prevent the proximal end portion 120 of the tubular member 108 from moving distally with respect to the protuberance 134 of the elongated member 102). The motion limiting mechanism(s) can establish a motion limit stop beyond which distal motion of the actuator conduit 162, outer conduit 154, and tubular member 108, as a coupled unit, are restrained relative to the inner shaft 168. In the embodiment shown, such motion limiting mechanisms can be controlled by the control button 156. For example, actuation of the control button 156 can allow the actuator conduit 162, outer conduit 154, and tubular member 108 to be moved past the limit stop such that the proximal end portion 120 of the tubular member 108 can move distally over the protuberance 134 of the elongated member 102, thereby locking the clipping arms 104, 106 in the closed position. Thus, after the leaflet clip 100 has been clipped to the leaflets of a heart valve, the control button 156 can be actuated to allow distal motion of the actuator conduit 162, outer conduit 154, and tubular member 108 past the limit stop to lock the clipping arms 104, 106 in the closed position.

Proximal motion of the outer conduit 154 can also be limited by one or more controllable motion limiting mechanisms to reduce the risk of accidental release of the tubular member 108 from the actuator conduit 162 during positioning of the leaflet clip 100. In the embodiment shown, such motion limiting mechanisms can be controlled by the control button 158. For example, actuation of the control button 158 can allow the outer conduit 154 to be moved proximally with respect to the actuator conduit 162, thereby uncovering the tabs 163, 165, allowing them to resume their natural non-deflected shape and disengage from the tubular member 108. This can release the tubular member 108 from the delivery system 150. Thus, after final positioning of the leaflet clip 100 in a heart valve, the control button 158 can be actuated to allow proximal motion of the outer conduit 154 and release of the actuator conduit 162 from the tubular member 108.

As for the embodiment shown in FIG. 5, the delivery system 150 can further include an inner member, or shaft, 168 disposed coaxially within the actuator conduit 162 and coupled at one end to the proximal end portion 110 of the elongated member 102, and at the opposite end to a handle member 170. In the embodiment shown, the inner member 168 can be coupled to the proximal end portion 110 of the elongated member 102 by threads such that rotation of the handle member 170 in the direction indicated by arrow 172 can uncouple the inner member 168 from the elongated member 102. For example, the distal end portion of the inner member 168 can have male threads that threadably engage female threads formed on an inner surface of the proximal end portion 110 of the elongated member 102. In this manner, after final positioning of the leaflet clip 100 in a heart valve, the actuator member 162 can be disengaged from the tubular member 108, the inner member 168 can be disengaged from the elongated member 102, and the delivery system 150 can be retracted, leaving the leaflet clip 100 in place.

In some embodiments, the diameter of the outer conduit 154 can be about ten French, and the system 150 can be configured for use with a guide wire (for example, threaded through the lumen 114 of the elongated member 102). In some embodiments, the respective conduits 154, 162 and the inner member 168 of the delivery system 150 can be flexible or rigid, as desired. In some embodiments, the delivery system 150 can include steering elements to aid in positioning and orienting the leaflet clip 100 with respect to a heart valve. Also, it should be understood that the respective conduits 154, 162 and the inner member 168 of the delivery system 150 are shown at reduced length for purposes of illustration, and can be any suitable length.

In use, the delivery system 150 can be introduced into a patient's vasculature (e.g., via the femoral artery or other suitable access point) and percutaneously advanced to the patient's heart with the clipping arms 104, 106 in the closed position (but not locked) using any of various delivery techniques. In a transfemoral procedure, the delivery device can be inserted through a femoral artery and the aorta to the heart in a retrograde direction (typically, but not exclusively used for deploying a clip on the leaflets of the aortic or mitral valves). Similarly, the delivery device can be inserted through a femoral vein and the vena cava to the right side of the heart in an antegrade direction (typically, but not exclusively used for deploying a clip on the leaflets of the pulmonary or tricuspid valves). In a transventricular procedure, the delivery device can be inserted through a surgical incision made in the chest and on the bare spot on the lower anterior ventricle wall (typically, but not exclusively used for deploying a clip on the leaflets of the aortic or mitral valves). Similarly, the delivery device can be inserted through a surgical incision on the wall of the right ventricle to access the pulmonary or tricuspid valves. In a transatrial procedure, the delivery device can be inserted through a surgical incision made in the wall of the left or right atrium to access the native valves on the left or right sides, respectively, of the heart. In a transaortic procedure, the delivery device can be inserted through a surgical incision made in the ascending aorta and advanced toward the heart (typically, but not exclusively used deploying a clip on the leaflets of the aortic or mitral valves). In a transeptal procedure, the delivery device can be advanced to the right atrium, such as via a femoral vein, and through the septum separating the right and left ventricles (typically, but not exclusively used for deploying a clip on the leaflets of the aortic or mitral valves). Further details of delivery techniques for accessing the native valves of the heart are disclosed in U.S. Patent Publication No. 2014/0067052, which is incorporated herein by reference.

Once located proximate the desired heart valve, the clipping arms 104, 106 are expanded by retracting the actuator conduit 162 to retract the tubular member 108 relative to the clipping arms 104, 106. The leaflet clip 100 can then be positioned with respect to a commissure of the valve, and can be distally advanced and/or retracted as needed to position the leaflet clip 100 such that one leaflet of the commissure is received in the first leaflet receiving region 128 and the second leaflet of the commissure is received in the second leaflet receiving region 130. When the leaflet clip 100 is suitably positioned, the actuator conduit 162 can be advanced such that the tubular member 108 moves distally with respect to the elongated member 102 and urges the clipping arms 104, 106 toward the closed position.

When the clipping arms are 104, 106 are in the closed position, the clipping strength of the leaflet clip 100 can be tested by pulling proximally on the delivery system 150. As used herein, the terms "clip retention force" and "clipping strength" refer to a force in the proximal direction that can be withstood by a leaflet clip without disengaging from the leaflets of a heart valve when the clipping arms are in the closed position. In some embodiments, the delivery system 150 can include a strain gauge or other device to measure the force applied to the leaflet clip 100. In some embodiments, the leaflet clip 100 can withstand a proximal force application of from between 1 N and about 10 N while remaining clipped to the valve leaflets. If, for example, the leaflet clip 100 is not suitably positioned, or the leaflet clip 100 does not exhibit suitable clipping strength when clipped to the leaflets, the tubular member 108 can be retracted by proximal motion of the actuator conduit 162, causing the clipping arms 104, 106 to reopen, and allowing the leaflet clip 100 to be repositioned. When the leaflet clip 100 is suitably positioned with respect to the valve leaflets, the actuator member 162 can advance the tubular member 108 distally of the protuberance 134, thereby locking the clipping arms 104, 106 in the closed position. The inner member 168 can then be disengaged from the elongated member 102, and the delivery system 150 can be retracted, leaving the leaflet clip 100 in place on the valve leaflets.

The leaflet clip 100, and any of the other leaflet clip embodiments described herein, can be used to treat valvular insufficiency or to remodel the annulus of a heart valve. For example, FIG. 11 illustrates three leaflet clips 202, 204, 206 similar to the leaflet clip 100 of FIG. 1 situated in a native aortic valve 200. The native aortic valve 200 can include three valve leaflets 210, 212, 214 attached to a valve annulus 216. The valve leaflets 210 and 212 can form a first commissure 218, the leaflets 212 and 214 can form a second commissure 220, and the leaflets 210 and 214 can form a third commissure 222. The leaflet clips 202, 204, 206 are shown situated at the first, second, and third commissures 218, 220, 222, respectively, such that the leaflet clip 202 engages the leaflets 210 and 212, the leaflet clip 204 engages the leaflets 212 and 214, and the leaflet clip 206 engages the leaflets 214 and 210. The leaflet clips 202, 204, 206 are also shown situated near the wall of the valve annulus 216. In this manner, the leaflet clips 202, 204, 206 can improve coaptation of the leaflets 210, 212, 214 at the respective commissures 218, 220, 222, thereby reducing regurgitation through the valve 200 due to valvular insufficiency. Additionally, although the leaflet clips 202, 204, 206 are shown clipped to the respective valve leaflets adjacent the annulus 216, the leaflet clips 202, 204, 206 can be clipped to the valve leaflets at any suitable location along the leaflets, including at the centers of the commissures, as desired.

The leaflet clips 202, 204, 206 can also remodel the annulus 216 of the valve 200 to reduce dilatation of the annulus 216 and/or to address abnormalities in the shape of the annulus 216. For example, FIG. 12 schematically illustrates remodeling of the annulus 216 to reduce its diameter from a dilated annulus diameter $D_1$ to a target or reduced annulus diameter $D_2$ using leaflet clips, such as the clips 202, 204, 206. Such remodeling or diameter reduction may be achieved by reducing the circumference of the annulus 216, as illustrated in FIGS. 13 and 14.

Figures 13, 14:
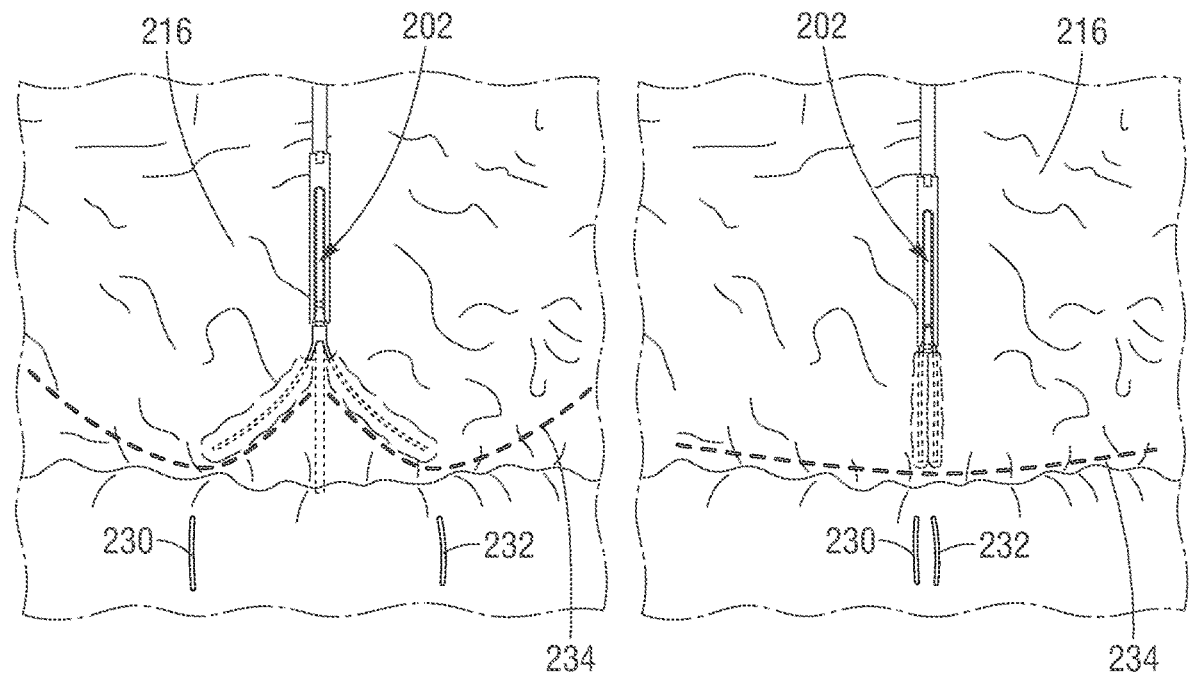
FIG. 13 is a side elevation view of a leaflet clip disposed in a heart valve with the clipping arms in the open position.
FIG. 14 is a side elevation view of the leaflet clip of FIG. 8 with the clipping arms in the closed position.

For example, FIG. 13 illustrates the leaflet clip 202 with its clip arms in the open position. Hash marks 230, 232 are shown on the tissue for purposes of indicating an initial distance between the clipping arms, as well as an initial reference for the circumference of the annulus. Dashed line 234 indicates the native contour of the valve cusp. FIG. 14 illustrates the leaflet clip 202 with its clip arms in the closed position such that the tissue of the annulus 216 adjacent the clip 202 is gathered and clipped together by the leaflet clip. This can reduce the circumference and, thereby, the diameter, of the annulus 216, as indicated by movement of the hash marks 230, 232 toward one another.

Figure 15:
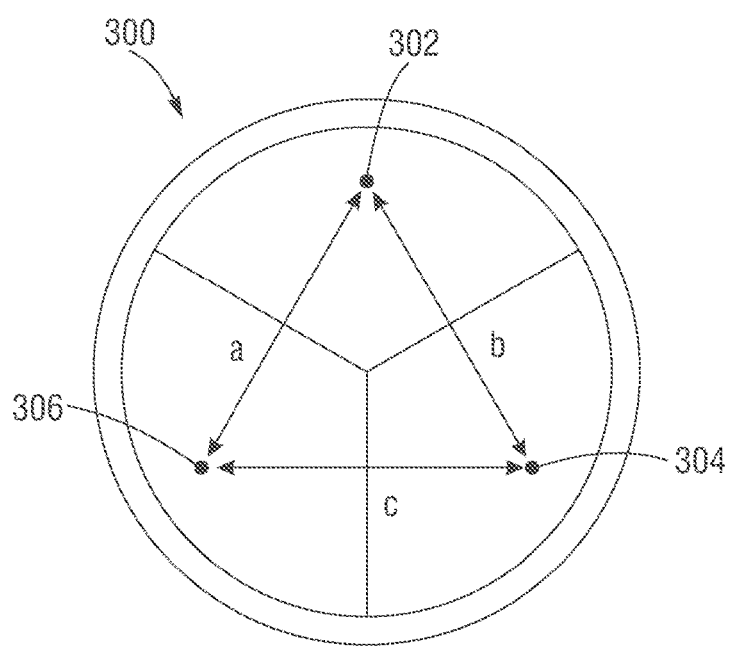
FIG. 15 is a schematic plan view of a heart valve illustrating distances between reference points on the walls of the valve annulus.
Figure 16:
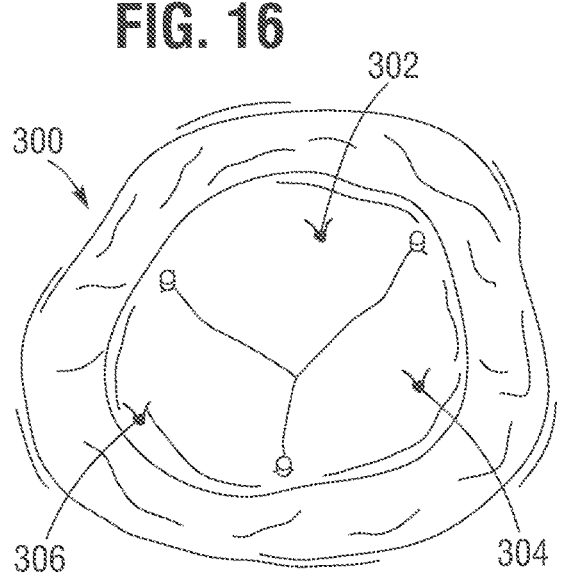
FIG. 16 is a cross-sectional plan view of a heart valve illustrating distances between reference points on the walls of the valve annulus prior to implantation of leaflet clips.
Figure 17:
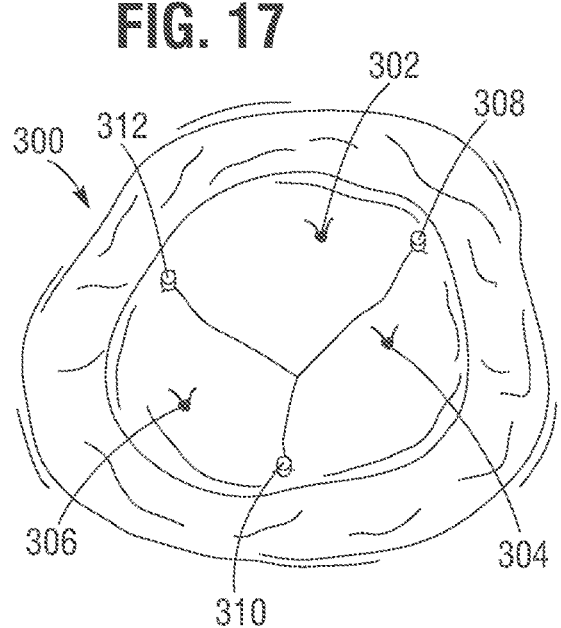
FIG. 17 is a cross-sectional plan view of the heart valve of FIG. 11 illustrating a reduction in diameter of the valve annulus after implantation of leaflet clips.

The effect of such a diameter reduction is further illustrated in FIGS. 15, 16, and 17, wherein the distances a, b, and c between three points 302, 304, 306 indicated schematically in FIG. 15, and illustrated on the annulus of a heart valve 300 in FIGS. 16 and 17, are reduced after application of three leaflet clips 308, 310, 312 to the commissures of the valve 300. In some embodiments, the diameter of the annulus can be reduced from a dilated diameter of about 29 mm to a target diameter of about 25 mm. In some embodiments, the diameter of the annulus can be reduced by from about 10% to about 50%. In some embodiments, the diameter of the annulus can be reduced by about 14%.

Figure 18:
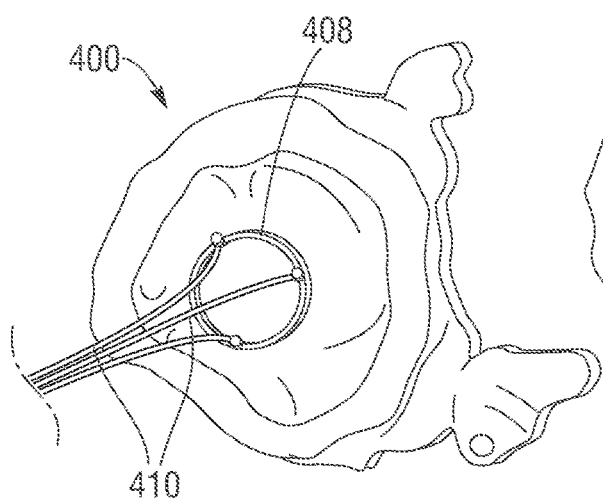
FIG. 18 is a cross-sectional view of the ventricular side of the aortic valve illustrating implantation of a support ring on three leaflet clips.
Figure 19:
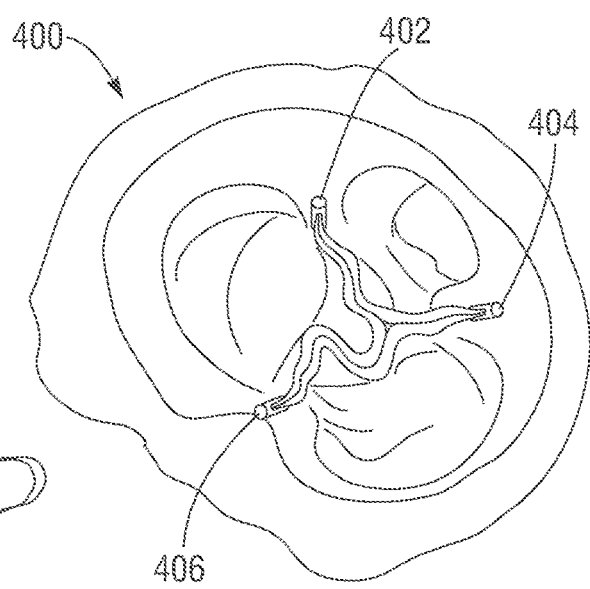
FIG. 19 is a cross-sectional view of the aortic side of the valve of FIG. 13 illustrating a reduction in diameter of the valve annulus with leaflet clips and the support ring.

Any of the leaflet clips disclosed herein can also be used in combination with one or more support rings, as shown in FIGS. 18 and 19. FIG. 19 illustrates three leaflet clips 402, 404, 406 clipped to the commissures of an aortic valve 400 as seen from the aortic root. FIG. 18 illustrates the location of a support ring 408 on the ventricular side of the aortic valve 400, which can cooperate with the leaflet clips 402, 404, 406 to remodel and/or reduce the diameter of the aortic valve 400, as shown in FIG. 19. The extensions 410 of the central shaft of each of the leaflet clips within the left ventricle can extend through respective openings of the ring 408 as shown. Alternatively, the ring 408 can be placed around the extensions 410. The leaflet clips 402, 404, 406, together with the support ring 408, or independent of any supporting device or structure, can also be used to achieve folding or plication of the commissures, as shown in FIG. 19.

Figure 20:
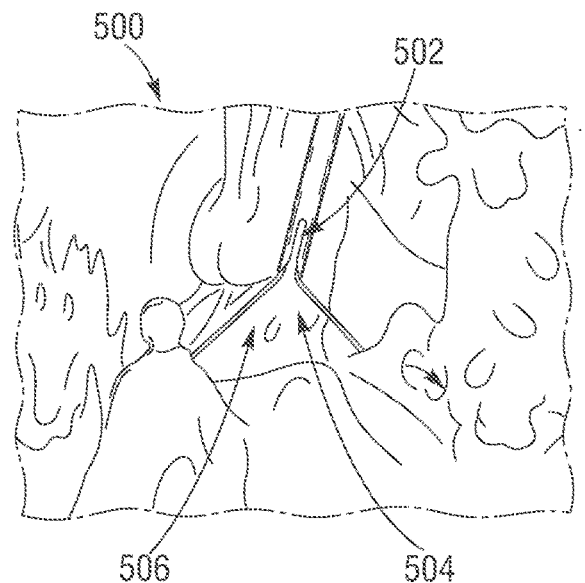
FIGS. 20 and 21 illustrate implantation of a leaflet clip into a mitral valve.
Figure 21:
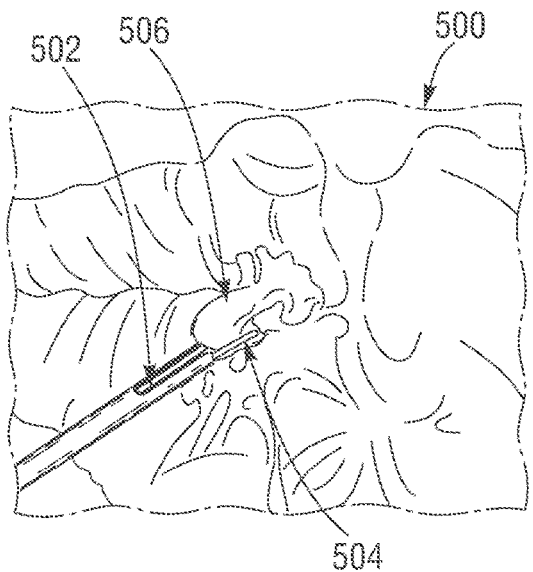

As stated above, any of the leaflet clips disclosed herein can also be used to treat valvular insufficiency or to remodel the annulus of the mitral valve and/or the tricuspid valve in addition to the aortic valve. FIGS. 20 and 21 illustrate placement of a leaflet clip 502 similar to the leaflet clip 100 of FIG. 1 onto the leaflets 504, 506 of a mitral valve 500. As illustrated in FIGS. 20 and 21, the relatively small width of the clip arms 508 of the leaflet clip 500 relative to the chordae of the mitral valve 500 can reduce interference by the clip arms 508 with the chordae both during implantation of the leaflet clip 502 and after implantation. In use, one or more leaflet clips 502 can be placed at or near the center of the leaflets 504, 506, or near the annulus, as desired.

Figure 22:
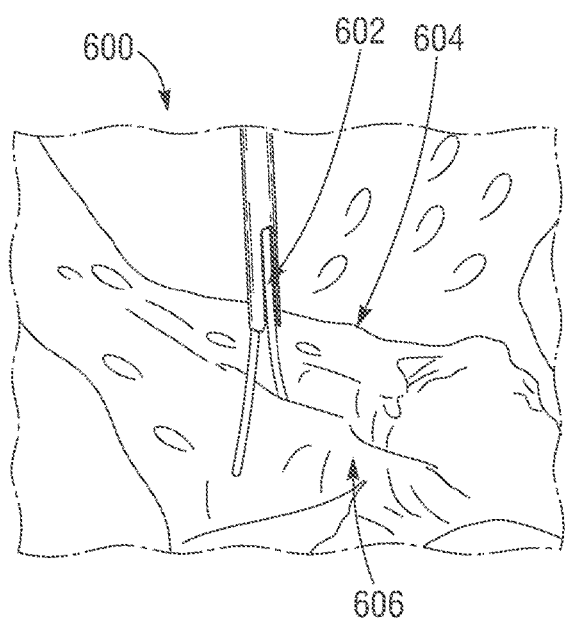
FIGS. 22 and 23 illustrate implantation of a leaflet clip into a tricuspid valve.
Figure 23:
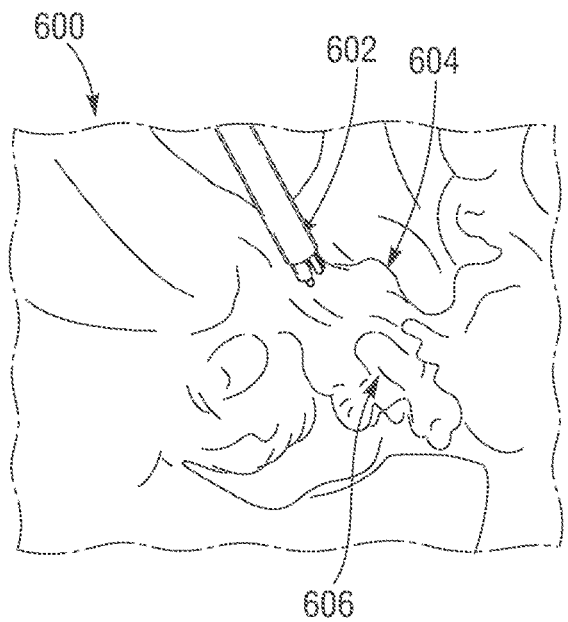

FIGS. 22 and 23 illustrate placement of a leaflet clip 602 similar to the leaflet clip 100 of FIG. 1 onto leaflets 604, 606 of a tricuspid valve 600. The leaflet clip 602, alone, or in combination with one or more additional leaflet clips, can be used to reduce valvular insufficiency and/or remodel the valve annulus, as described above.

FIGS. 24-32 illustrate various configurations of clipping arms that may be used in combination with any of the leaflet clips disclosed herein. Additionally, although the leaflet clips of FIGS. 24-26 are illustrated without central elongated members, it should be understood that any of the leaflet clips described herein can include an elongated member (e.g., member 102) or not, as desired. FIG. 24 illustrates a leaflet clip 700 wherein the clipping arms 702, 704 exhibit bends indicated at 702A and 704A, and extend outwardly without exhibiting any significant further curvature (i.e., the clipping arms 702, 704 are relatively straight).

FIG. 25 illustrates a leaflet clip 800 wherein the clipping arms 802, 804 exhibit two bends, the first bends being indicated at 802A, 804A, and the second bends indicated at 802B, 804B, respectively, such that the clipping arms 802, 804 include respective distal portions 806, 808 angled away from the tubular member 810 at an angle α greater than about 45 degrees.

FIG. 26 illustrates a leaflet clip 900 wherein the clipping arms 902, 904 have curved distal end portions 906, 908.

FIG. 27 illustrates a leaflet clip 1000 similar to the leaflet clip 800 of FIG. 25 wherein the clipping arms 1002, 1004 exhibit first bends indicated at 1002A, 1004A and second bends indicated at 1002B, 1004B such that distal portions 1006, 1008 of the clipping arms 1002, 1004 are angled away from the tubular member 1010 at an angle α less than about 45 degrees.

FIG. 28 illustrates a leaflet clip 1100 wherein the clipping arms 1102, 1104 extend distally adjacent the elongated member 1106 before bending away from the elongated member 1106 such that the areas of the respective leaflet receiving regions 1108, 1110 are reduced.

FIGS. 29 and 30 illustrate an embodiment of a clipping arm 1600 including one or more openings 1602 defined in the clipping arm 1600. The clipping arm 1600 can include openings 1602 located at the distal end portion of the clipping arm 1600, as shown in FIG. 29, or spaced apart along the length of the clipping arm 1600, as shown in FIG. 30. The clipping arm 1600 can include a fibrous covering or sleeve 1604, which can be disposed around the distal end portion of the clipping arm 1600, as in FIG. 29, or along the entire length of the clipping arm 1600, as shown in FIG. 30. The covering 1604 can be retained on the clipping arm 1600 by suture threads 1606, which can be disposed about the covering 1604 and received or laced through the plurality of openings 1602 in order to retain the covering 1604 on the clipping arm 1600. In this manner, the covering 1604 can serve to frictionally engage the tissue of the leaflets of a heart valve while reducing the risk of damage to the leaflets. In alternative embodiments, the clipping arm 1600 can include any suitable number of openings 1602 located at any suitable location along the length of the clipping arm, and can include a covering extending along any suitable proportion of the clipping arm 1600, as desired. The covering 1604 can be made from a suitable biocompatible fabric, such as PET.

FIG. 31 illustrates another embodiment of a clipping arm 1700 including a proximal end portion 1702 and a distal end portion 1704. In the embodiment shown, clipping arm 1700 can be tapered such that the proximal end portion 1702 has a first diameter or width $W_1$ and the distal end portion 1704 has a second diameter or width $W_2$, the first diameter $W_1$ being greater than the second diameter $W_2$. This can allow the distal end portion 1704 a greater degree of flexibility relative to the proximal end portion 1702 in the directions indicated by arrow 1706, which can reduce the risk of damage to the tissue of native heart valve leaflets. The distal end portion 1704 can also include a protuberance 1708 having a relatively large diameter relative to the diameter $W_2$ of the distal end portion 1704, which can reduce the risk of puncturing the native leaflets during or after implantation of the leaflet clip.

FIG. 32 illustrates another embodiment of a clipping arm 1800 including an inner member 1802 and an over-molded covering 1804 (i.e., an "insert molding"). The covering 1804 can be fabricated from any biocompatible polymer (e.g., silicone, ePTFE, etc.), and can include texturing, dimpling, or other surface features to aid in engaging and retaining the tissue of a native valve leaflet. The inner member 1802 can be fabricated from metal or polymer materials, as desired.

Figure 33:
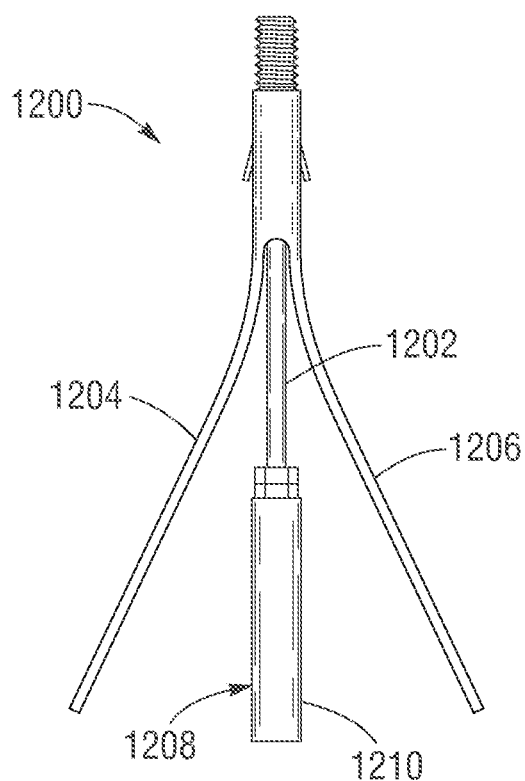
FIG. 33 illustrates another embodiment of a leaflet clip including a passive leaflet engaging mechanism.

FIG. 33 illustrates another embodiment of a leaflet clip 1200 similar to the leaflet clip 100 of FIG. 1. The leaflet clip 1200 can include an elongated member 1202 and two clipping arms 1204, 1206. The leaflet clip 1200 is illustrated without a tubular member (sheath) for purposes of illustration. The leaflet clip 1200 can include a passive leaflet engaging mechanism configured as a tube or sleeve 1208 and disposed on a distal end portion 1210 of the elongated member 1202. The sleeve 1208 can be made from, for example, polyester, and can be configured to frictionally engage and retain the leaflets of a heart valve between the respective clipping arms 1204, 1206 and the elongated member 1202 as the clipping arms are moved from the open position to the closed position.

Figure 34:
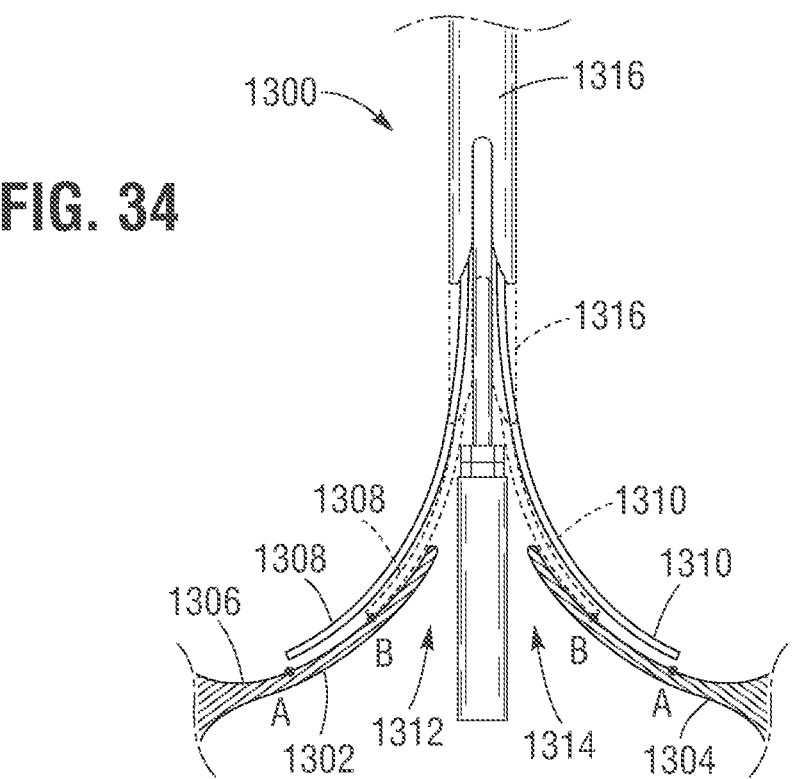
FIG. 34 illustrates movement of the leaflets of a heart valve with respect to the clipping arms of a leaflet clip as the clipping arms are moved from an open position to a closed position.

FIG. 34 schematically illustrates the relative positions of the native leaflets 1302, 1304 of a heart valve 1306 relative to the clipping arms 1308, 1310 of a leaflet clip 1300 before and after the clipping arms 1308, 1310 are moved from the open position to the closed position. In a manner similar to leaflet clip embodiments described above, distal motion of a tubular member 1316 from a first position (indicated in solid lines) to a second position (indicated in phantom) can cause the clipping arms 1308, 1310 to move from the open position to the closed position. When the leaflets 1302, 1304 are received in the respective leaflet receiving regions 1312, 1314, the ends of the clipping arms 1308, 1310 can contact the leaflets 1302, 1304 at respective points A along the respective leaflets 1302, 1304. In some embodiments, as the clipping arms 1308, 1310 are moved from the open position to the closed position, the leaflets 1302, 1304 can slip such that when the clipping arms 1308, 1310 are in the closed position, they contact the leaflets 1302, 1304 at respective points B. Depending upon the degree of gripping strength desired, it may be advantageous, in certain circumstances, to retain a greater proportion of the leaflets 1302, 1304 in the leaflet receiving regions 1312, 1314 as the clipping arms are moved from the open position to the closed position.

Figure 35:
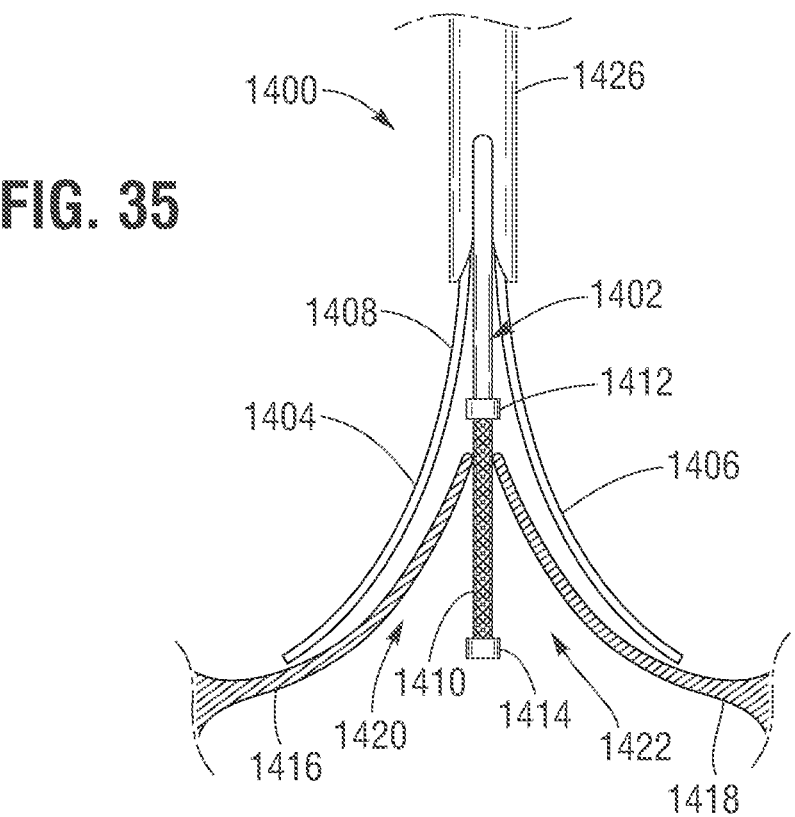
FIG. 35 is a side elevation view of another embodiment of a leaflet clip including a movable and expandable covering illustrated in a distal position.
Figure 36:
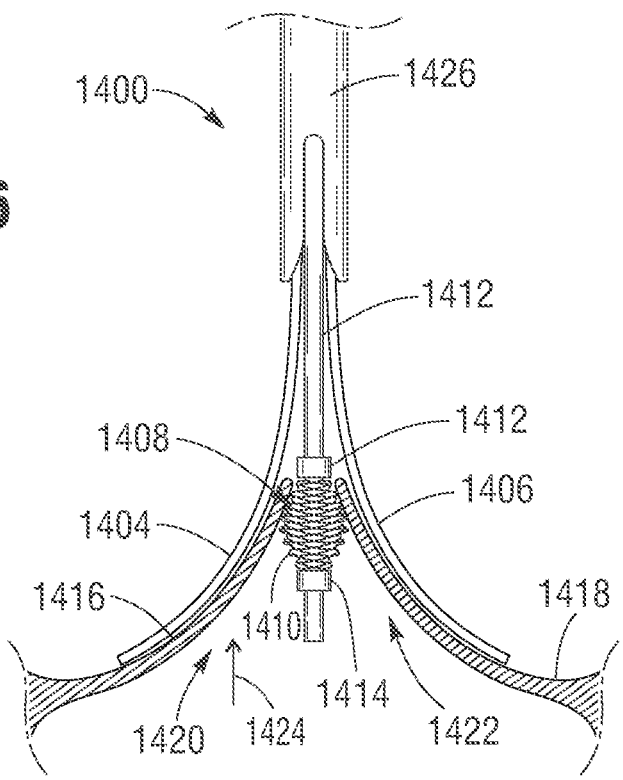
FIG. 36 is a side elevation view the leaflet clip of FIG. 26 illustrating the active leaflet engaging mechanism in a proximal position in an expanded configuration.

To such ends, FIGS. 35 and 36 illustrate another embodiment of a leaflet clip 1400 including an elongated member 1402 and two clipping arms 1404, 1406. The leaflet clip 1400 can include an active leaflet engaging mechanism 1408 configured as a woven or braided covering 1410 disposed on the elongated member 1402 between a stationary proximal retaining member 1412 and a distal retaining member 1414 movable between a distal position and a proximal position. When the leaflet clip 1400 is positioned such that native leaflets 1416, 1418 are received in the respective leaflet receiving regions 1420, 1422, the distal retaining member 1414 can be moved proximally in the direction indicated by arrow 1424 of FIG. 36 (e.g., by actuation of a member disposed within the elongated member 1402). Motion of the distal retaining member 1414 toward the proximal retaining member 1412 can cause the covering 1410 to bunch such that it expands or bulges radially away from the elongated member 1402 and engages the leaflets 1416, 1418 between the covering 1410 and the respective clipping arms 1404, 1406. When the distal retaining member 1414 is in the proximal position, the tubular member 1426 can be advanced distally such that the clipping arms 1404, 1406 are moved from the open position to the closed position. In this manner, retention of the leaflets 1416, 1418 in the respective leaflet receiving regions 1420, 1422 while the clipping arms 1404, 1406 are moved to the closed position can result in a greater proportion of the leaflets being retained against the elongated member 1402 by the leaflet clip 1400, resulting in a stronger grip on the leaflets and improved performance of the leaflet clip 1400. Additionally, the leaflet engaging mechanism 1408 can reduce slippage of the leaflets 1416, 1418 past the clipping arms 1404, 1406 as they moved to the closed position, helping to ensure that a greater proportion of the leaflets 1416, 1418 are retained in the leaflet receiving regions 1420, 1422 and increasing retention of the leaflet clip 1400 on the leaflets 1416, 1418.

Figure 37:
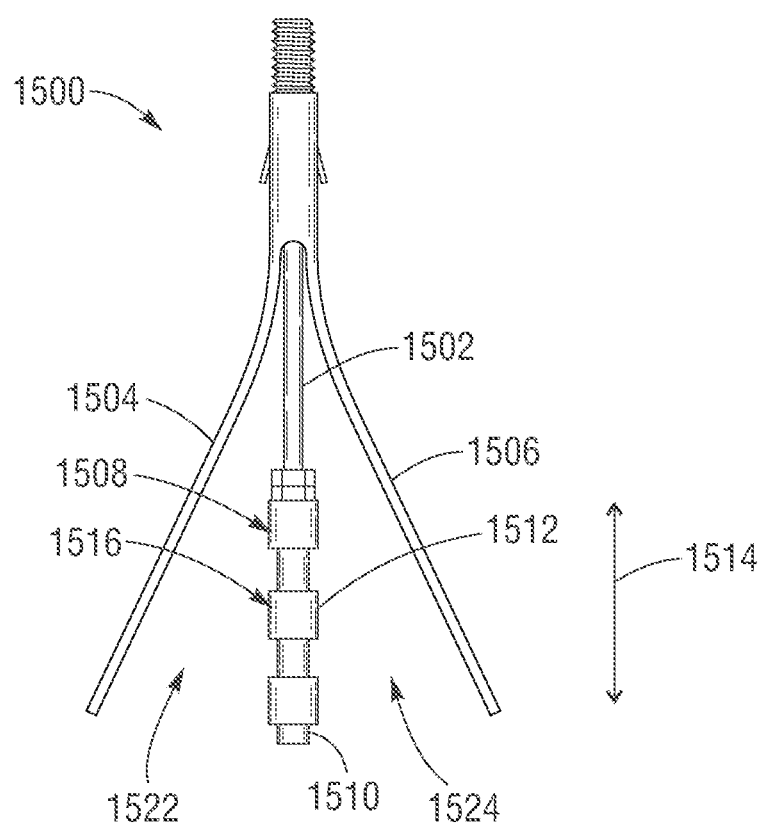
FIGS. 37 and 38 are side elevation views of another embodiment of a leaflet clip including an active leaflet engaging mechanism including a plurality of protuberances.
Figure 38:
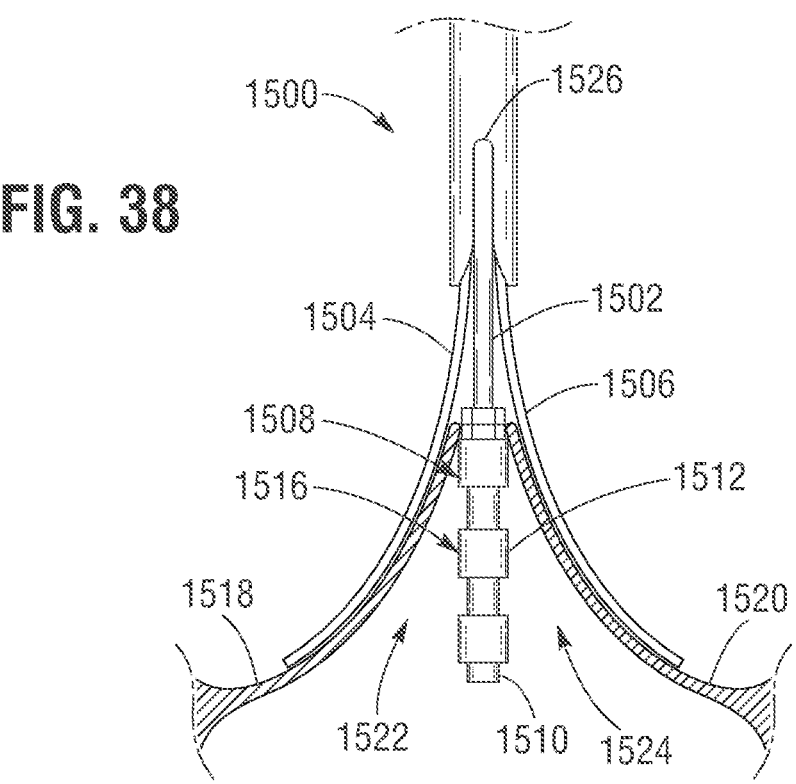

FIGS. 37 and 38 illustrate another embodiment of a leaflet clip 1500 including an elongated member 1502, two clipping arms 1504, 1506, and a sheath 1526. The leaflet clip 1500 can include an active leaflet engaging mechanism 1508 configured as a sleeve 1510 including a plurality of protuberances 1512 axially spaced apart from one another along the sleeve 1510. The sleeve 1510 can be movable between a distal position and a proximal position relative to the clipping arms 1504, 1506, as indicated by arrow 1514 (FIG. 37). The protuberances 1512 can have respective edge portions 1516 configured to engage or grip native leaflets 1518, 1520 disposed in respective leaflet receiving regions 1522, 1524 when the sleeve 1510 is moved proximally, as depicted in FIG. 38. Thus, when the clipping arms 1504, 1506 are moved to the closed position (e.g., by advancing the sheath 1526 over the clipping arms), the edge portions 1516 of the protuberances 1512 can engage and retain the leaflets 1518, 1520 within the leaflet receiving regions 1522, 1524, thereby inhibiting the leaflets from slipping out of the leaflet receiving regions. This can result in a greater proportion of the leaflets 1518, 1520 being retained against the elongated member 1502 by the clipping arms 1504, 1506, resulting in a stronger grip on the leaflets and improved performance of the leaflet clip 1500.

In the embodiment shown, the sleeve 1510 includes three protuberances 1512. However, it should be understood that the sleeve 1510 can include any suitable number of protuberances having any suitable size and spacing relative to one another. In some embodiments, the sleeve 1510 can be disposed on the elongated member 1502, which can be movable proximally and/or distally. In alternative embodiments, the sleeve 1510 can be disposed on a shaft or conduit coaxially disposed within (or over the exterior) of the elongated member 1502 and independently actuated from outside the body. In some embodiments, the sleeve 1510 can be made from suitable natural or synthetic material, such as, for example, polyester. In some embodiments, the spaces between the protuberances 1512 can act as tissue gathering regions (see description regarding FIGS. 42-46), helping to increase the clipping strength of the leaflet clip 1500.

FIGS. 39 and 40 schematically illustrate alternative coupling orientations of leaflet clips with respect to delivery systems. In FIG. 39, a leaflet clip 1900 is shown coupled to a delivery system 1902 with clipping arms 1904, 1906 extending distally with respect to the delivery system 1902. FIG. 40 illustrates a leaflet clip 2000 coupled to a delivery system 2002 with the clipping arms 2004, 2006 extending proximally with respect to the delivery system 2002. It should be understood that these coupling orientations may be applied to any of the leaflet clips described herein, and can facilitate the various delivery techniques described above.

FIG. 41 illustrates another embodiment of a leaflet clip 2100 coupled to a delivery system 2102 such that clipping arms 2104, 2106 extend proximally with respect to the delivery system 2102, similar to the embodiment of FIG. 40. The leaflet clip 2100 can include a tubular member 2108 disposed coaxially about an elongated member 2110, and movable between a distal position and a proximal position such that the clipping arms 2104, 2106 are urged by the tubular member 2108 from an open position to a closed position, respectively. The tubular member 2108 can be coupled to an actuator member 2112 via a coupling device 2114, illustrated as a threaded connection between the distal end of the tubular member 2108 and the actuator member 2112. The actuator member 2112 can extend coaxially through the elongated member 2110, and can be movable with respect to the elongated member 2110 in the direction indicated by arrow 2113 such that proximal or distal motion of the actuator member 2112 causes corresponding proximal or distal motion of the tubular member 2108.

The elongated member 2110 can be coupled to an inner conduit 2116 by tabs 2118, 2120 received in respective openings 2122, 2124 of the elongated member 2110. The tabs 2118, 2120 can be retained in the openings 2122, 2124 by an adjacent outer conduit 2126 coaxially disposed about the inner conduit 2116 and configured such that an inner surface of the outer conduit 2126 contacts and urges or deflects the tabs 2118, 2120 into the openings 2122, 2124 of the elongated member 2110. In this manner, the leaflet clip 2100 can remain coupled to the delivery system 2102 while allowing proximal and distal motion of the actuator member 2112 and the tubular member 2108 to facilitate positioning and/or repositioning of the clipping arms 2104, 2106.

In the embodiment shown, the elongated member 2110 can include tabs or extension portions 2128, 2130 near the distal end of the elongated member 2110, which can be received in corresponding openings 2132, 2134 defined in the tubular member 2108. In this manner, after final positioning of the leaflet clip, the actuator member 2112 can be moved proximally with respect to the elongated member 2110 such that tubular member 2108 deflects the clipping arms 2104, 2106 into the closed position and the tabs 2128, 2130 are received in the openings 2132, 2134 of the tubular member 2108, thereby locking the tubular member 2108 in the proximal position and, thereby, locking the clipping arms 2104, 2106 in the closed position. The outer conduit 2126 can then be moved proximally in the direction of arrow 2136, allowing the tabs 2118, 2120 of the inner conduit 2116 to disengage from the elongated member 2110. The actuator member 2112 can then be rotated, for example, in the direction indicated by arrow 2138 such that the threaded coupling 2114 between the actuator member 2112 and the tubular member 2108 is disengaged. The delivery system 2102 may then be withdrawn, leaving the leaflet clip 2100 in place.

Figure 43:
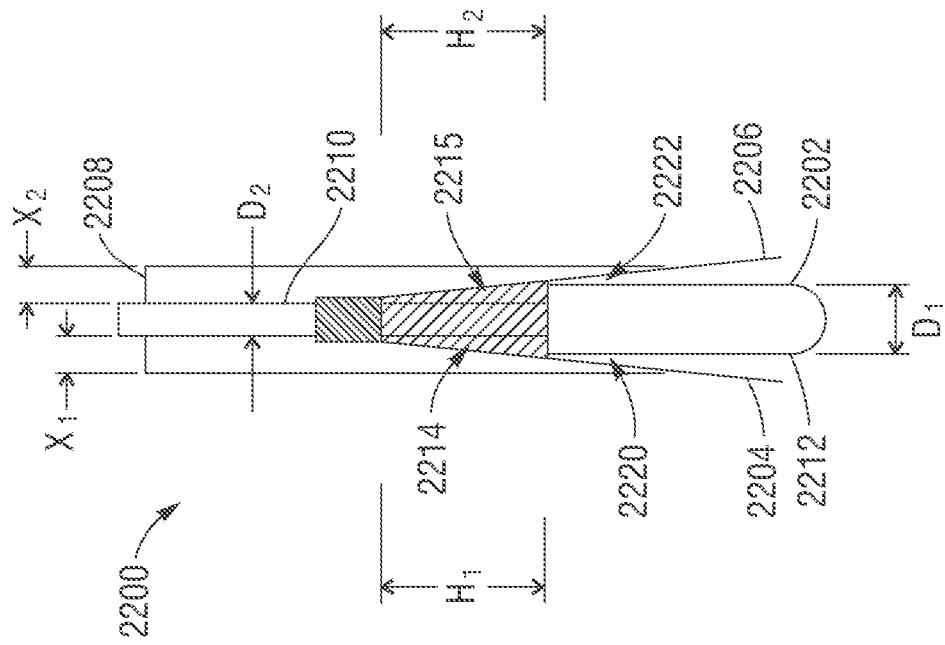
FIGS. 42 and 43 illustrate another embodiment of a leaflet clip including tissue gathering regions.
Figure 42:
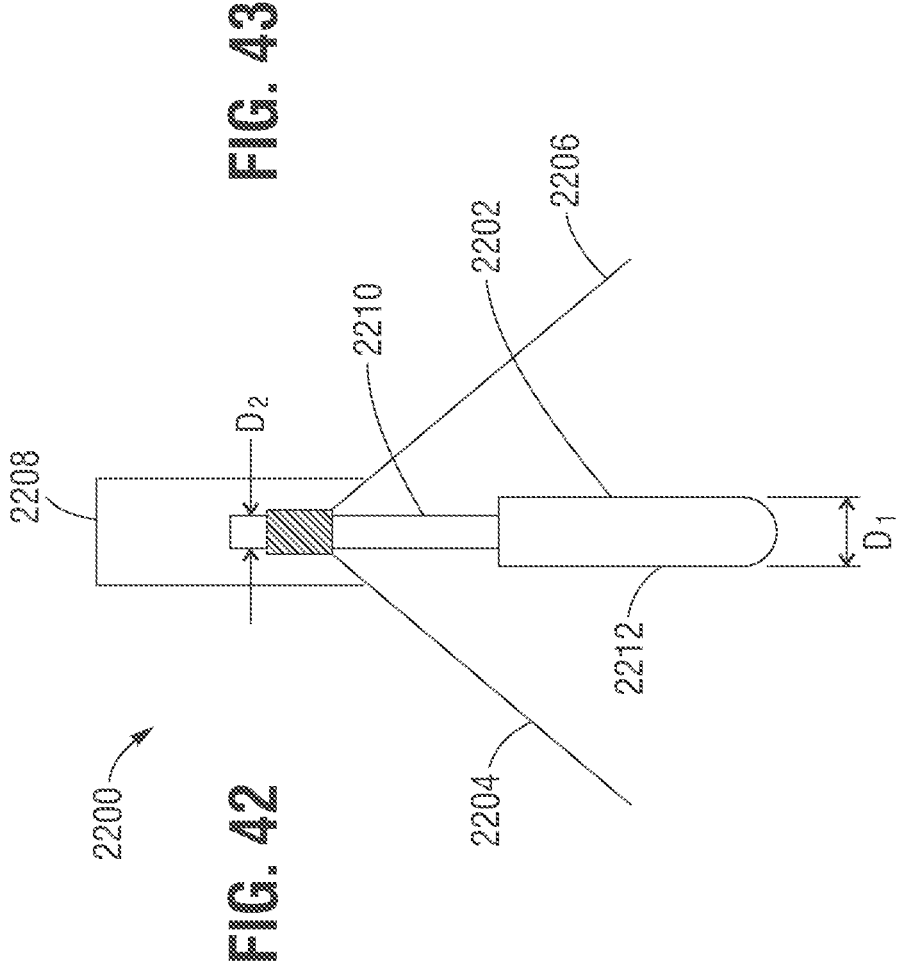

FIGS. 42 and 43 illustrate another embodiment of a leaflet clip 2200 including an elongated member 2202, first and second clipping arms 2204, 2206, and a tubular member 2208 disposed coaxially with respect to the elongated member 2202. The elongated member 2202 can have a proximal end portion 2210 and a distal end portion 2212, with the distal end portion 2212 having a diameter $D_1$ that is greater than a diameter $D_2$ of the proximal end portion 2210. In this manner, the clipping arms 2204, 2206 can define respective tissue gathering regions 2214, 2215 between the respective clipping arms 2204, 2206 and the elongated member 2202 when the clipping arms are in the closed position, as shown in FIG. 43. In the embodiment shown, the tissue gathering regions 2214, 2215 can have respective width dimensions $X_1$ and $X_2$, and height dimensions $H_1$ and $H_2$. In some embodiments, the width dimensions $X_1$ and $X_2$ can vary along the height of the respective tissue gathering regions due to, for example, the angle between the respective clipping arms 2204, 2206 and the elongated member 2202, and/or flexion in the clipping arms 2204, 2206 when they are in the closed position.

The clipping arms 2204, 2206 can also define respective tissue compression regions 2220, 2222 between the clipping arms 2204, 2206 and the elongated member 2202 having respective width dimensions $W_1$ and $W_2$. In some embodiments, the dimensions $W_1$ and $W_2$ can vary along the length of the respective tissue compression regions 2220, 2222 due to the angle between the respective clipping arms 2204, 2206 and the elongated member 2202, and/or flexion in the clipping arms 2204, 2206, as described above.

The tissue gathering regions 2214, 2215 can be located adjacent the proximal end portion of the elongated member 2202, and can be configured such that the end portions of the native leaflets of a heart valve extend into the tissue gathering regions 2214, 2215. In the tissue gathering regions 2214, 2215, the tissue of the free end portions of the leaflets can gather or bunch, while the lower portions of the leaflets can be simultaneously engaged or pinched between the clipping arms 2204, 2206 and the elongated member 2202 in the tissue compression regions 2220, 2222. This can result in a difference between the thickness of the leaflet tissue in the tissue gathering regions 2214, 2215, where the tissue is relatively unconfined and/or not compressed, and the thickness of the leaflet tissue disposed in the tissue compression regions 2220, 2222. This difference in thickness can significantly increase the clipping strength of the leaflet clip 2200, thereby increasing the leaflet clip's ability to remain clipped to the leaflets of a working heart valve.

For example, FIGS. 44 and 45 schematically illustrate the mechanics of the tissue gathering regions and the tissue compression regions. In FIG. 44, the free end portion 2304 of a leaflet 2302 is pinched between a clipping arm 2306 and an elongated member 2308 of a leaflet clip 2300. In an unconstrained state, the leaflet 2302 can have a thickness T, and the leaflet clip 2300 can be configured such that the clipping arm 2306 and the elongated member 2308 define a tissue compression region 2310 (corresponding to the tissue compression regions 2220, 2222 of FIGS. 42 and 43) having a dimension D when the clipping arm 2306 is in the closed position. In a typical example, the distance D between the elongated member 2308 and the clipping arm 2306 can be configured to compress the tissue of the leaflet 2302 such that the thickness T of the leaflet tissue is reduced by about 50% relative to the thickness of the unconstrained tissue. Thus, for a valve leaflet having a thickness T of about 1 mm, the tissue compression region 2310 can be configured to compress the tissue disposed in the region 2310 such that its thickness T is reduced to about 0.5 mm. This ratio of thickness reduction can generally result in greater retention of the leaflet tissue between the clipping arm 2306 and the elongated member 2308, while minimizing the risk of damage to the leaflet 2302.

As stated above, FIG. 44 illustrates the free end portion 2304 of the leaflet 2302 disposed in the tissue gathering region 2310. In a typical example, such an arrangement can withstand a proximal force application of approximately 1 N. However, by configuring the leaflet clip 2300 such that the free end portion 2304 of the leaflet 2302 is relatively unconstrained, such as when disposed in a tissue gathering region, while a mid-portion 2312 of the leaflet 2302 is compressed in the tissue compression region 2310, the clipping strength of the leaflet clip can be significantly increased. FIG. 45 schematically illustrates such an arrangement, wherein the mid-portion 2312 of the leaflet 2302 is pinched in the leaflet compression region 2310 such that its thickness is reduced to about 0.5 T, while the free end portion 2304 of the leaflet 2302 is disposed in a tissue gathering region 2314 and allowed to maintain its natural thickness T. In some embodiments, this arrangement can allow the leaflet clip 2300 to withstand a proximal force application of about 4 N, which can significantly improve the clipping strength of the leaflet clip. Use of features such as the tissue gathering regions 2214, 2215 can also promote long-term stability of the leaflet clip 2200 after implantation by fostering tissue growth in tissue gathering regions 2214, 2215 and around the clip 2200.

Returning to the leaflet clip 2200, FIG. 46 illustrates the leaflet clip 2200 with the clipping arms 2204, 2206 in the closed position with leaflets 2216, 2218 captured in the tissue compression regions 2220, 2222. The tissue compression regions 2220, 2222 can be configured such that the portions of the leaflets 2216, 2218 disposed in the regions 2220, 2222 can be compressed such that their respective thicknesses T are reduced to about 0.5 T, as described above. Meanwhile, the tissue gathering regions 2214, 2215 can be configured such that the free end portions 2224, 2226 of the leaflets 2216, 2218 are allowed to maintain to their natural thickness T, which can significantly increase the clipping strength of the leaflet clip 2200.

In some embodiments, the width dimensions $X_1$, $X_2$ and the height dimensions $H_1$, $H_2$ of the tissue gathering regions 2214, 2215, and/or the width dimensions $W_1$, $W_2$ of the tissue compression regions 2220, 2222 can be sized according to the thickness T of the valve leaflets 2218, 2220. For example, in some embodiments, the width dimensions $X_1$, $X_2$ of the tissue gathering regions 2214, 2215 can be from about 1 T to about 2 T. In some embodiments, the width dimensions $X_1$, $X_2$ of the tissue gathering regions 2214, 2215 can be about 1 T. In some embodiments, the height dimensions $H_1$, $H_2$ of the tissue gathering regions 2214, 2215 can be from about 1 T to about 2 T. In some embodiments, the width dimensions $W_1$, $W_2$ of the tissue compression regions 2220, 2222 can be about 0.5 T, as described above.

FIG. 47 illustrates another embodiment of a leaflet clip 2400 including a tubular central member 2402 having a proximal end portion 2404 and a distal end portion 2406. The distal end portion 2406 can include first and second clipping arms 2408, 2410 movable between an open position and a closed position. The clipping arms 2408, 2410 can define a leaflet receiving region 2411 therebetween, which can receive leaflets 2416, 2418 of a heart valve. The leaflet clip 2400 can also include a tubular exterior member 2412 disposed coaxially about the central member 2402 and movable between a proximal position and a distal position relative to the central member 2402. The exterior member 2412 can be configured such that as it is moved from the proximal position to the distal position, an interior surface of the exterior member 2412 contacts the clipping arms 2408, 2410 and urges or deflects them from the open position to the closed position.

The leaflet clip 2400 can also include a helical member 2414, illustrated in the shape of a corkscrew. The helical member 2414 can be disposed within the lumen of the central member 2402, and can be movable between a proximal position and distal position relative to the central member 2402. In this manner, when the leaflets 2416, 2418 are received in the leaflet receiving region 2411 and the clipping arms 2408, 2410 are in the closed position, the helical member 2414 can be advanced distally through the lumen of the central member 2402 to engage the leaflets 2416, 2418. This can result in plication of the leaflets 2416, 2418, and improve the clipping strength of the leaflet clip 2400. In some embodiments, the helical member 2414 can pierce the leaflets 2416, 2418, or can engage the leaflets 2416, 2418 without piercing them, as desired. In some embodiments, the helical member 2414 can also include a detachable coupling mechanism 2420 for coupling the leaflet clip 2400 to a delivery device.

Figure 48:
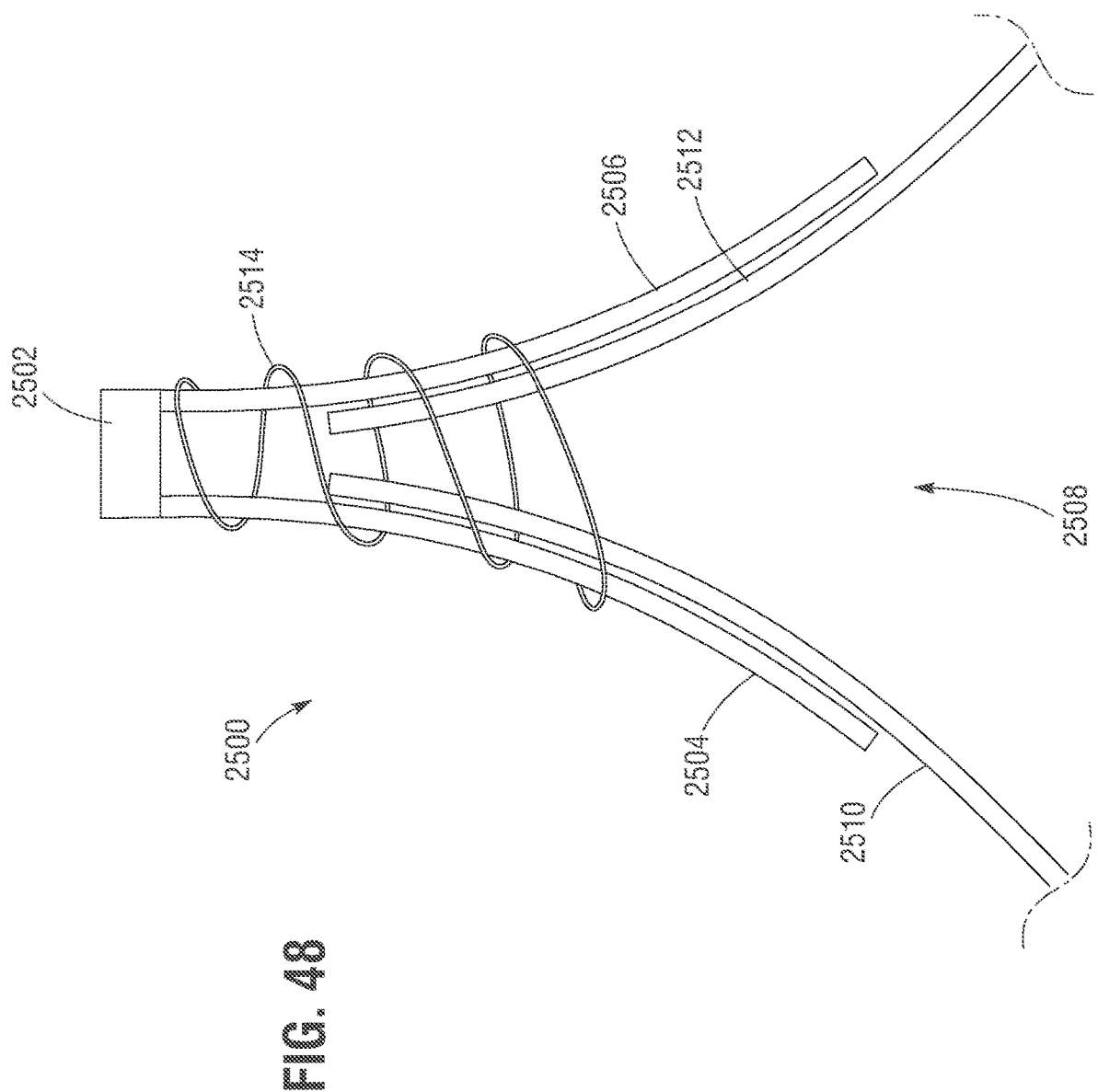
FIG. 48 illustrates another embodiment of a leaflet clip including a helical member disposed about the clipping arms.

FIG. 48 illustrates another embodiment of a leaflet clip 2500 including a central member 2502 with two clipping arms 2504, 2506 extending distally therefrom. The clipping arms 2504, 2506 can be movable between an open position and a closed position, and can define a leaflet receiving area 2508, which can receive leaflets 2510, 2512. The leaflet clip 2500 can further include a helical member 2514, which can be movable between a proximal position and a distal position. In some embodiments, the helical member 2514 can comprise, for example, a spirally wound metal wire. When the helical member 2514 is in the distal position, it can be disposed around the clipping arms 2510, 2512 and configured to restrain radial movement of the clipping arms 2504, 2506 with respect to one another. In this manner, the helical member 2514 can retain the leaflets 2510, 2512 between the clipping arms 2504, 2506, thereby retaining the leaflet clip 2500 on the heart valve.

FIGS. 49 and 50 illustrate another embodiment of a delivery device 2600 that can be used in combination with any of the leaflet clips described herein. The delivery device can include a handle body 2602 including a proximal handle portion 2604 and a distal handle portion 2606. The delivery device can further comprise an outer conduit 2608 coupled to the distal handle portion 2606, and an intermediate or clip release conduit 2610 disposed coaxially within the outer conduit 2608 and coupled to the proximal handle portion 2604. The clip release conduit 2610 can be movable proximally and distally relative to the outer conduit 2608 with proximal and distal motion of the proximal handle portion 2604. The delivery device can further include a clip retention conduit 2612 disposed coaxially within the clip release conduit 2610 and coupled to the distal handle portion 2606. In the illustrated embodiment, the clip retention conduit 2612 can include tab portions 2614, 2616 (FIG. 50) that engage openings in a tubular member 2618 of the leaflet clip 2620 when covered and deflected inwardly by the clip release conduit 2610, similar to the embodiment of FIGS. 1-10 above.

The delivery device can also include an inner shaft or conduit 2622 (FIG. 40) disposed coaxially within the clip retention conduit 2612. The inner shaft 2622 can be coupled to a proximal end portion of the central elongated member 2624 (FIG. 50) of the leaflet clip such that proximal and distal motion of the inner shaft 2622 causes corresponding proximal and distal motion of the elongated member 2624 relative to the tubular member 2618. By moving the central elongated member 2624 of the leaflet clip relative to the tubular member 2618, the clip arms 2626, 2628 can be drawn proximally into the tubular member 2618 and deflected such that the clip arms are moved to the closed position, or pushed distally from the tubular member such that the clip arms return to their non-deflected, open state. Alternatively, the inner shaft 2622 can be coupled to the tubular member 2618 such that longitudinal motion of the inner shaft causes corresponding longitudinal motion of the tubular member to open and close the clip arms.

In the illustrated embodiment, the inner shaft 2622 can also include a handle portion 2630 for effecting proximal and distal motion of the inner shaft. The inner shaft 2622 can also define a lumen that is in communication with a lumen of the elongated member 2624 for receiving a guide wire. The handle portion 2602 can also include a locking feature to prevent inadvertent separation of the proximal and distal handle portions (e.g., during shipment).

In the illustrated embodiment, the clip release conduit 2610 can include a pin or projection 2632 movable with the clip release conduit in a track or guide 2634 defined in the outer conduit 2608. In the illustrated embodiment, the guide 2634 can include a circumferentially extending distal portion 2636, a longitudinally extending intermediate portion 2638, and a longitudinally extending proximal portion 2640 circumferentially offset from the intermediate portion, although other configurations are possible.

When the device is inserted into the body and advanced toward the heart, the proximal and distal handle portions 2604, 2606 can be adjacent one another, and the clip release conduit 2610 can be distally disposed such that the projection 2632 is in the distal portion 2636 of the guide 2634 and the leaflet clip is located within the lumen of the clip release conduit. When the distal end of the device reaches the desired implantation site, the proximal handle portion 2604 can be rotated, causing corresponding rotation of the clip release conduit 2610. This can cause the projection 2632 of the clip release conduit to move into the intermediate portion 2638 of the guide 2634. The proximal handle portion 2604 can then be pulled proximally or retracted such that the proximal handle portion separates from the distal handle portion 2606, causing corresponding proximal movement of the clip release conduit 2610 and of the projection 2632 in the intermediate portion 2638 of the guide. The clip release conduit 2610 can be retracted a sufficient distance to expose the clip arms of the leaflet clip 2620, but not so far that the tabs 2614, 2616 of the clip retention conduit are exposed and allowed to open and release the leaflet clip from the delivery device.

The leaflet clip 2620 can then be clipped onto and/or released from the native leaflets of the target heart valve by proximal and distal motion of the inner shaft 2622. When a suitable placement of the leaflet clip on the native leaflets has been achieved, the clip arms 2626, 2628 can be locked in the closed position. The proximal handle portion 2604 can then be rotated such that the projection 2632 moves into the distal portion 2640 of the guide 2634. This allows the handle portion 2604 to be moved further in the proximal direction such that the clip release conduit 2610 uncovers the tabs 2614, 2616 of the clip retention conduit 2612, releasing the leaflet clip from the delivery device.

The delivery device illustrated in FIGS. 49 and 50 can be adapted for use with a transapical delivery procedure. However, it should be understood that the device of FIGS. 49 and 50 can be adapted for use with any suitable delivery procedure, including transfemoral procedures, transatrial procedures, transeptal procedures, etc.

In view of the many possible embodiments to which the principles of the disclosed technology may be applied, it should be recognized that the illustrated embodiments are only preferred examples and should not be taken as limiting the scope of the disclosure. Rather, the scope of the disclosure is defined by the following claims.

We claim:

1. A valve repair system comprising:
 a clip for attachment to two leaflets of a heart valve comprising:
  an elongated member configured to be positioned between the two leaflets of the heart valve;
  a pair of arms that are coupled to a first end portion of the elongated member;

wherein the pair of arms extend radially away from the elongated member as the pair of arms extend away from the first end portion toward a second end portion when the arms are in an open position;

a delivery system comprising:

an actuator member that extends into the second end portion of the elongated member and through the elongated member such that a distal end of the actuator is past the second end portion of the elongated member;

a conduit releasably coupled to the second end portion of the elongated member;

wherein movement of the distal end of the actuator member toward the conduit moves the pair of arms from an open position to a closed position.

2. The system of claim 1 further comprising a tubular member connected to the distal end of the actuator member and configured to move the pair of arms from the open position to the closed position.

3. The system of claim 1 wherein the end of the distal end of the actuator member is threaded.

4. The system of claim 1 wherein the distal end of the actuator member is threaded into a component of the clip to attach the clip to the actuator member.

5. The system of claim 1 wherein the conduit is coupled to the second end portion of the elongated member by tabs that are deflected radially inward.

6. The system of claim 5 wherein the conduit is released from the elongated member by releasing the tabs to allow the tabs to move radially outward.

7. The system of claim 1 wherein the end of the actuator member is threaded into a component of the clip to attach the clip to the actuator member and the conduit is coupled to the second end portion of the elongated member by tabs that are deflected radially inward.

8. The system of claim 7 wherein the clip is released from the delivery system by unthreading the actuator member from the component of the clip and by releasing the tabs to allow the tabs to move radially outward.

9. The system of claim 7 wherein the component of the clip includes an annular threaded end.

10. The system of claim 7 wherein the component of the clip comprises a tubular member.

11. The system of claim 1 wherein the width of the second portion of the elongated member is greater than the width of the first portion of the elongated member.

12. A clip for attachment to two leaflets of a heart valve comprising:

an elongated member configured to be positioned between the two leaflets of the heart valve;

an expandable covering disposed over the elongated member;

wherein the expandable covering is configured to expand radially away from the elongated member;

a pair of arms that are coupled to a first end portion of the elongated member;

wherein the pair of arms extend radially away from the elongated member as the pair of arms extend away from the first end portion toward a second end portion when the arms are in an open position;

wherein the pair of arms are moveable from the open position to a closed position; and wherein the expandable covering is made from a woven or braided material.

13. A clip for attachment to two leaflets of a heart valve comprising:

an elongated member configured to be positioned between the two leaflets of the heart valve;

an expandable covering disposed over the elongated member;

wherein the expandable covering is configured to expand radially away from the elongated member;

a pair of arms that are coupled to a first end portion of the elongated member;

wherein the pair of arms extend radially away from the elongated member as the pair of arms extend away from the first end portion toward a second end portion when the arms are in an open position;

wherein the pair of arms are moveable from the open position to a closed position; and wherein the expandable material is disposed between a proximal retaining member and a distal retaining member.

14. The clip of claim 13 wherein the distal retaining member is moveable toward the proximal retaining member to radially expand the expandable covering.

15. A clip for attachment to two leaflets of a heart valve comprising:

an elongated member configured to be positioned between the two leaflets of the heart valve;

an expandable covering disposed over the elongated member;

wherein the expandable covering is configured to expand radially away from the elongated member;

a pair of arms that are coupled to a first end portion of the elongated member;

wherein the pair of arms extend radially away from the elongated member as the pair of arms extend away from the first end portion toward a second end portion when the arms are in an open position;

wherein the pair of arms are moveable from the open position to a closed position; and a tubular member configured to move the pair of arms from the open position to the closed position.

* * * * *